(12) United States Patent
Moriyama

(10) Patent No.: US 6,203,494 B1
(45) Date of Patent: Mar. 20, 2001

(54) ENDOSCOPE CAPABLE OF VARYING HARDNESS OF FLEXIBLE PART OF INSERTION UNIT THEREOF

(75) Inventor: Hiroki Moriyama, Akishima (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/260,760

(22) Filed: Mar. 2, 1999

(51) Int. Cl.[7] ....................................... A61B 1/00
(52) U.S. Cl. ................ 600/144; 600/149; 600/150; 604/525
(58) Field of Search ..................... 600/144, 149, 600/150; 604/525, 526, 527

(56) References Cited

U.S. PATENT DOCUMENTS

| | | | |
|---|---|---|---|
| 4,329,980 | * 5/1982 | Terada | 128/4 |
| 4,928,669 | * 5/1990 | Sullivan | 128/4 |
| 4,977,887 | * 12/1990 | Gouda | 128/4 |
| 5,125,395 | * 6/1992 | Adair | 128/4 |
| 5,810,715 | 9/1998 | Moriyama | 600/144 |
| 5,885,208 | * 3/1999 | Moriyama | 600/144 |
| 5,976,074 | * 11/1999 | Moriyama | 600/144 |

FOREIGN PATENT DOCUMENTS 3-43802    4/1991    (JP) .

* cited by examiner

Primary Examiner—Linda C. M. Dvorak
Assistant Examiner—Jocelyn Debra Ram
(74) Attorney, Agent, or Firm—Ostrolenk, Faber, Gerb & Soffen, LLP

(57) ABSTRACT

An endoscope capable of varying the hardness of a soft part of an insertion unit thereof includes a hardness adjustment unit and a location changing mechanism. The hardness adjustment unit includes an elongated coil and a wire lying through the coil, and adjusts the hardness of the soft part of the insertion unit. The location changing mechanism changes relatively the location of the coil and wire in a longitudinal direction of the insertion unit to maintain the hardness adjustment unit such that the insertion unit is hardened most greatly.

17 Claims, 13 Drawing Sheets

ENDOSCOPE CAPABLE OF VARYING HARDNESS OF FLEXIBLE PART OF INSERTION UNIT THEREOF

BACKGROUND OF THE INVENTION

1. Field of the Invention

The present invention relates to an endoscope having a hardness adjusting means for adjusting the hardness of a flexible part of an insertion unit thereof.

2. Description of the Related Art

In recent years, endoscopes by which various kinds of therapies and treatments can be conducted have been widely adopted. An elongated insertion unit of such an endoscope is inserted into the body cavity, whereby a region to be tested in the body cavity is observed without an incision. If necessary, a treatment appliance may be passed through a treatment appliance channel in the endoscope.

The insertion unit of the endoscope is flexible so as to be inserted into a bent body cavity. However, since the insertion unit has plasticity, it becomes difficult to reliably convey manipulations, which are performed at the proximal part of the insertion unit, to the distal part thereof. This leads to the deteriorated ability of the distal part of the insertion unit to respond to manipulations performed at the proximal part thereof. Consequently, a problem arises in that since the direction of the distal part is not determined, it becomes hard to insert the insertion unit smoothly into an intended region.

For overcoming the problem, for example, Japanese Unexamined Utility Model Publication No. 3-43802 has disclosed an endoscope having a hardness adjusting means (or a hardness varying means) incorporated therein. The hardness adjusting means is composed of an elongated coil and wire. An operator who conducts an endoscopic examination performs a simple manipulation to adjust the plasticity of the flexible part of the insertion unit. This makes it easy to insert the insertion unit into a bent channel.

The hardness adjusting means has a elongated coil and a wire lying through the elongated coil. Both ends of the coil and wire are firmly fixed by brazing to bases formed at both ends of a flexible tube serving as armor of a plastic tube of an endoscope.

If the hardness adjusting means is used repeatedly, the elongated coil deteriorates. The natural length thereof may be shortened. In this case, if the wire were pulled, the distal end of the flexible tube would be pulled more greatly than it is pulled before the elongated coil deteriorated. An unnecessarily large load may then be imposed on the flexible tube. Consequently, there arises a fear that the flexible tube will be twisted or will deteriorate.

Moreover, when the hardness adjusting means is driven forcefully, the elongated coil may be buckled or the wire may be broken. Otherwise, the coil or wire may deteriorate significantly. In this case, it becomes impossible to replace the coil or wire with a new one.

SUMMARY OF THE INVENTION

The present invention provides an endoscope capable of varying the hardness of a flexible part of an insertion unit thereof. Herein, when the function of a hardness adjusting means deteriorates because of repeated use, the function is corrected to thus sustain the quality of the flexible part.

The present invention also provides an endoscope capable of varying the hardness of a flexible part of an insertion unit thereof in which a hardness adjusting means that is easily replaceable is incorporated.

Briefly, an endoscope capable of varying the hardness of a flexible part of an insertion unit thereof in accordance with the present invention comprises a hardness adjusting means and a location changing means. The hardness adjusting means includes an elongated coil and a wire lying through the coil, and adjusts the hardness of the flexible part of the insertion unit of the endoscope. When the hardness adjusting means is adjusted to the position providing the greatest hardness, the location changing means relatively changes the location of the coil and wire located in a longitudinal direction of the insertion unit.

BRIEF DESCRIPTION OF THE DRAWINGS

FIG. 1 to FIG. 13 are diagrams for explaining the first embodiment of the present invention;

FIG. 1 is a diagram for explaining the configuration of an endoscopic system;

FIG. 2 is a lateral sectional view for explaining the structures of a linkage member for linking a bendable part and plastic tube and its surroundings;

FIG. 3 is a longitudinal sectional view for explaining the structures of the linkage member linking the bendable part and plastic tube and its surroundings;

FIG. 4 is a sectional view for explaining the structure of a front-end part of an operation unit;

FIG. 5 is a 5—5 sectional view of the structure shown in FIG. 4;

FIG. 6 is a 6—6 sectional view of the structure shown in FIG. 5;

FIG. 7 shows the structure shown in FIG. 6 and seen from the direction 7 in FIG. 6;

FIG. 8 is a diagram for explaining the portion 8 shown in FIG. 4;

FIG. 9 is a diagram for explaining a spacer;

FIG. 10 is a 10—10 sectional view of the structure shown in FIG. 4;

FIG. 11 is a 11—11 sectional view of the structure shown in FIG. 4;

FIG. 12 is a diagram for explaining the structure and operation of cam grooves;

FIG. 13A is a diagram showing a scene where an insertion unit is passed into the anus, passed through the rectum, and inserted into the sigmoid colon;

FIG. 13B is a diagram showing a scene where the distal part of the insertion unit has reached near the curved portion of the spleen;

FIG. 13C is a diagram showing a scene where the distal part of the insertion unit has passed through the transverse colon, gone beyond the curved portion of the liver, and reached the cecum;

FIG. 14 to FIG. 19 are diagrams to be referred to for explaining the second embodiment;

FIG. 14A is a longitudinal sectional view for explaining the structures of the linkage member linking the bendable part and plastic tube and it surroundings;

FIG. 14B is a 14B—14B sectional view of the structures shown in FIG. 14A;

FIG. 14C is a longitudinal sectional view for explaining structures of the linkage member linking the bendable part and plastic tube and surroundings;

FIG. 14D is a 14D—14D sectional view of the structures shown in 14C;

FIG. 15 is a sectional view for explaining the structure of the front-end part of an operation unit;

FIG. 16A is a 16A—16A sectional view of the structure shown in FIG. 15;

FIG. 16B is a 16B—16B sectional view of the structure shown in FIG. 15;

FIG. 17 is a diagram showing a C-shaped ring;

FIG. 18A is a diagram showing one practical example of cam grooves;

FIG. 18B is a diagram showing another practical example of cam grooves;

FIG. 19A is a diagram for explaining initial work for replacing the hardness adjustment unit with a new one;

FIG. 19B is a diagram showing a scene where a string coupled to a linkage member is passed through a flexible tube;

FIG. 19C shows a scene where a linkage member of a new hardness adjustment unit is coupled to the distal end of the string;

FIG. 19D shows a scene where the new hardness adjustment unit has been passed through the flexible tube;

FIG. 20 is a diagram for explaining a structure for mounting the distal part of a hardness adjustment unit; and FIG. 21 is a diagram explaining the structure for mounting the back-end part of the hardness adjustment unit.

DESCRIPTION OF THE PREFERRED EMBODIMENTS

Referring to FIG. 1 to FIG. 13, the first embodiment of the present invention will be described below.

Figure 1:
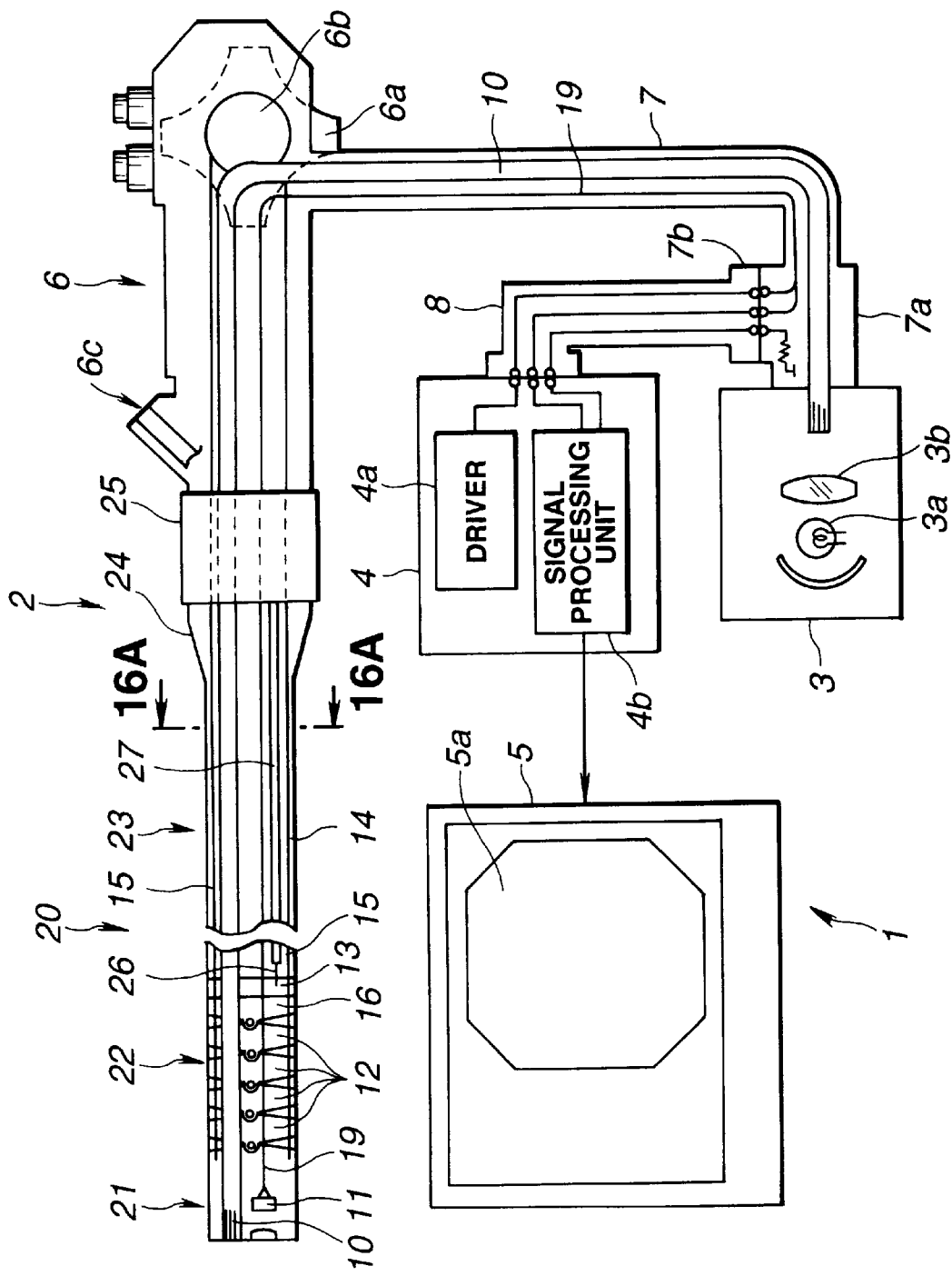

As shown in FIG. 1, an electronic endoscope system 1 of this embodiment consists mainly of an electronic endoscope 2, a light source apparatus 3, a signal processing apparatus 4, and a monitor 5. The electronic endoscope 2 has a solid-state imaging device such as a CCD 11 incorporated in a distal part 21 of an elongated insertion unit 20. The light source apparatus 3 has an illumination lamp 3a and a condenser 3b incorporated therein. The illumination lamp 3a and condenser 3b are used to supply illumination light over a light guide cable 10 lying through the electronic endoscope 2. The signal processing apparatus 4 includes a driver 4a and a signal processing unit 4b. The driver 4a drives the CCD 11. The signal processing unit 4b converts an image signal transmitted from the CCD 11 into a video signal. The monitor 5 includes a display device 5a for displaying an image according to the video signal produced by the signal processing unit 4b.

The insertion unit 20 of the electronic endoscope 2 consists of a distal part 21, a bendable part 22, and a plastic tube 23. The distal part 21 has the CCD 11 incorporated therein. The bendable part 22 made by concatenating a plurality of joint sections communicates with the distal part 21. The plastic tube 23 includes a flexible tube 14 providing a flexible soft part that communicates with the bendable part 22 via a linkage tube 13.

An operation unit 6 having an angling knob 6a for angling the bendable part 22 is attached to the back end of the insertion unit 20. The angling knob 6a is manipulated by an operator. A drum 6b included in the operation unit 6 is turned by manipulating the angling knob 6a. An angling wire 15 wound about the drum 6b is pulled duly, whereby the bendable part 22 is angled in a desired direction.

A universal cord 7 extends from the flank of the operation unit 6. A light source connector 7a detachably attached to the light source apparatus 3 is coupled to the back end of the universal cord 7. An electric connector 7b is formed on the flank of the light source connector 7a. An external cable 8 that can be uncoupled freely is coupled to the electric connector 7b and signal processing apparatus 4. The signal processing apparatus 4 and CCD 11 are thus connected over a signal line 19.

The back end of the insertion unit 20 of the electronic endoscope 2 and the front end of the operation unit 6 are joined via an anti-breakage member 24. A hardness adjustment knob 25 that is substantially cylindrical abuts the front end of the operation unit 6, and adjoins the anti-breakage member 24. The hardness adjustment knob 25 is manipulated to cause a hardness adjusting means, which will be described later, to adjust hardness.

The hardness adjustment knob 25 is turned to operate on a hardness adjustment wire (hereinafter, a wire) 26 and a metallic coil hardness adjustment coil (hereinafter, a coil) 27. The wire 26 is an integral part of the hardness adjusting means lying through the plastic tube 23, and has plasticity. The coil 27 is wound densely in the form of a pipe. Thus, the hardness (or plasticity) of the plastic tube 23 is adjusted.

The wire 26 is passed through the coil 27. A treatment appliance insertion port 6c communicates with a treatment appliance channel over which a treatment appliance or the like are routed to a body cavity.

Figure 2:
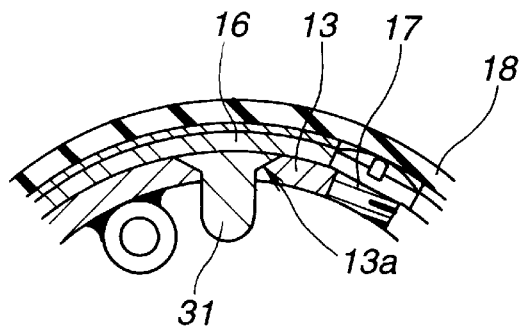
Figure 3:
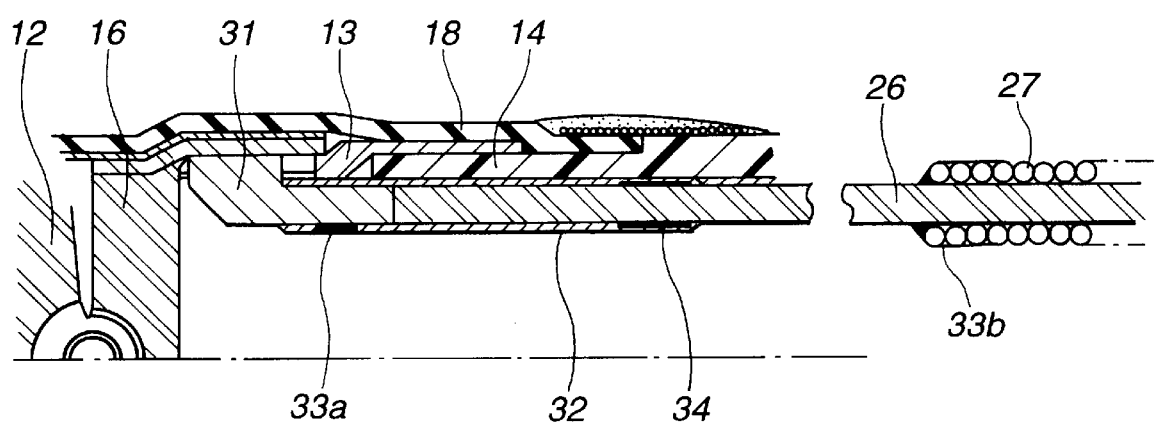

As shown in FIG. 2 and FIG. 3, the linkage tube 13 linking the bendable part 22 and plastic tube 23 is secured b a screw 17. The linkage tube 13 is engaged with a back-end joint section 16 located at the backmost end of the plurality of joint sections 12 constituting the bendable part 22.

Moreover, the linkage tube 13 has a notch 13a in which a linkage member 31 is fitted. The linkage member 31 is locked in the notch 13a. Consequently, when the linkage tube 13 and back-end joint section 16 are secured unitedly, the linkage member 31 projects from the linkage tube 13 towards the hollow of the endoscope.

On the other hand, when the screw 17 is removed and the back end joint section 16 and linkage tube 13 are separated from each other, the linkage member 31 can be slid and freed from the linkage tube 13. An armor tube 18 serves as an outer layer of the bendable part 22. Moreover, the screw 17 may be inserted into one point or a plurality of points.

As shown in FIG. 3, one end of a linkage pipe 32 is fitted on part of the linkage member 31. The linkage pipe 32 and the linkage member 31 are thus securely united by a brazing filler 33.

The distal part of the wire 26 is inserted into the linkage pipe 32 through the other end of the linkage pipe 32. The wire 26 is locked by a solder 34. Moreover, the distal part of the coil 27 is fixed firmly to the distal part of the wire 26, which extends from the linkage pipe 32, by the brazing filler 33. The fixture between the wire 26 and the linkage pipe 32 is not limited to the solder 34 but may be caulking or an adhesive.

Figure 4:
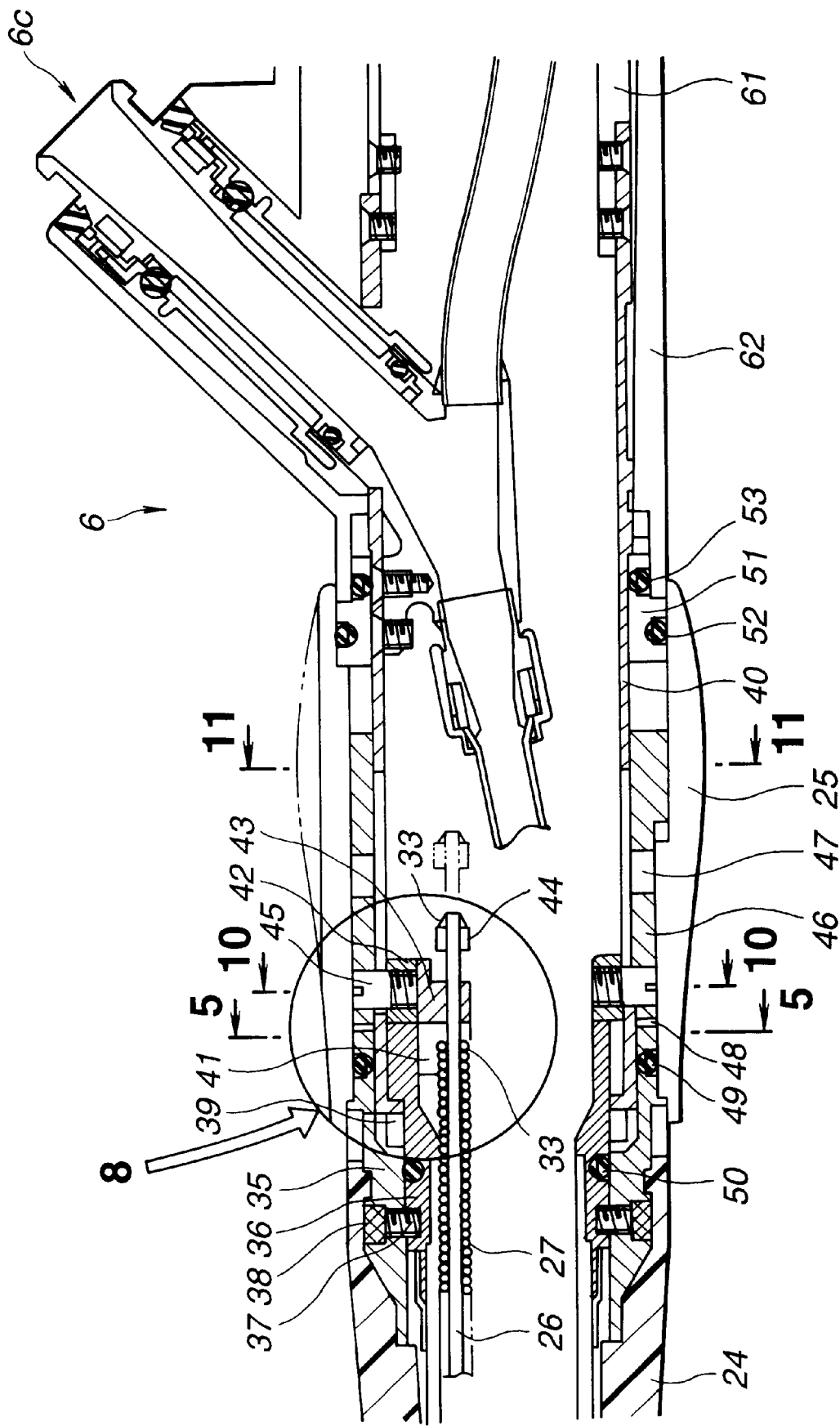

Referring to FIG. 4, the structure of the front-end part of the operation unit 6 will be described.

As illustrated, a support member 35 is press-fitted on the back end of the anti-breakage member 24. A back-end base 36 is placed on the inner circumference of the support member 35. The back-end base 36 is fixed to the support member 35 by screws 37. The heads of the screws 37 are locked in holes bored in the support member 35. The holes are filled with a filler 38.

The back-end base 36 is attached to the front-end part of a cylindrical tube 40 by a screw ring 39. The front-end part of the cylindrical tube 40 is fixed to an operation unit body 61 forming the operation unit 6. Moreover, a coil stopper 41 is mounted on the inner circumference of the back-end base 36. The back end of the coil 27 is locked in the coil stopper 41. Furthermore, a movable ring 42 is placed adjacent the back-end base 36 within the cylindrical tube 40. A pull member 43 is attached to the movable ring 42.

The back end of the wire 26 passes through the coil 27, a through hole bored in the coil stopper 41, and a groove cut in the pull member 43, and projects into the operation unit 6. A wire stopper 44 for preventing the projecting wire 26 from coming off is fixed firmly to the back-end portion of the wire 26 by the brazing filler 33.

Moreover, the back end of the coil 27 is locked firmly in the coil stopper 41 by the brazing filler 33.

Movable pins 45 are embedded in locations on the movable ring 42 where the movable pins are mutually symmetrical with respect to the center axis of the movable ring 42. The movable pins 45 are engaged with cam grooves 47 cut in a cam ring 46 placed on the outer circumference of the cylindrical tube 40.

Figure 11:
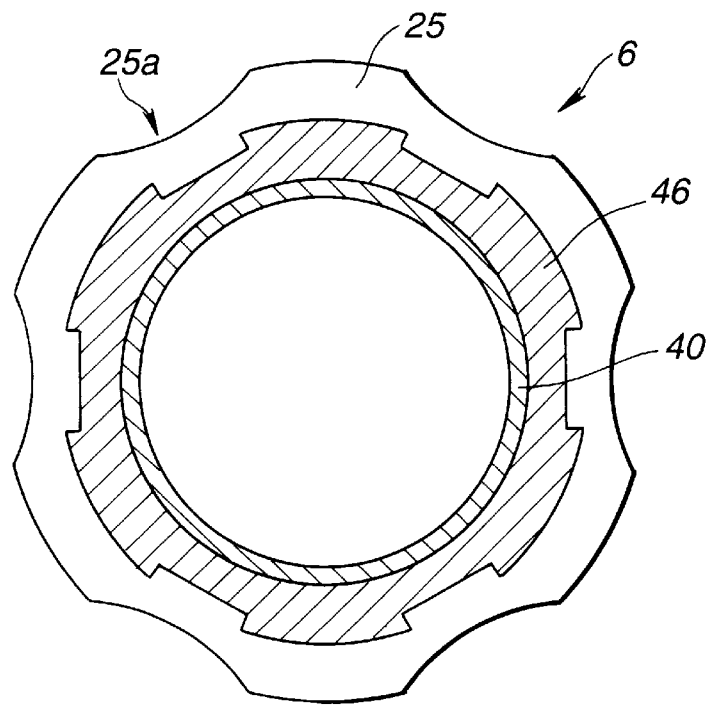

The hardness adjustment knob 25 is overlaid on the outer circumference of the cam ring 46. As shown in FIG. 11 to be referred to later, the concave and convex parts of the cam ring and hardness adjustment knob are meshed with one another. This restricts the direction of turning.

Moreover, a sliding ring 48 is interposed between the front end of the cam ring 46 and the back end of the back-end base 36. The back-end base 36 and cam ring 46 are made of the same material. The sliding ring 48 is made of a material whose hardness is different from that of the material made into the back-end base 36 and cam ring 46. This is intended to prevent the back-end base 36 and cam ring 46 sticking when they slide.

Furthermore, a first seal ring 49 embedded in the support member 35 comes into close contact with the inner circumference of the front-end part of the hardness adjustment knob 25. Watertightness is thus maintained.

The back-end base 36 and support member 35 are sustained in a watertight manner by means of a second seal ring 50.

Moreover, the rear part of the hardness adjustment knob is overlaid on a seal receiving member 51. Watertightness between the hardness adjustment knob 25 and seal receiving member 51 is maintained by a third seal ring 52 embedded in the seal receiving member 51.

In addition, the front-end part of a cylindrical body 62 is overlaid on the back-end part of the receiving member 51. Watertightness between the receiving member 51 and cylindrical body 62 is maintained by a fourth seal ring 53 embedded in the cylindrical body 62.

Figure 5:
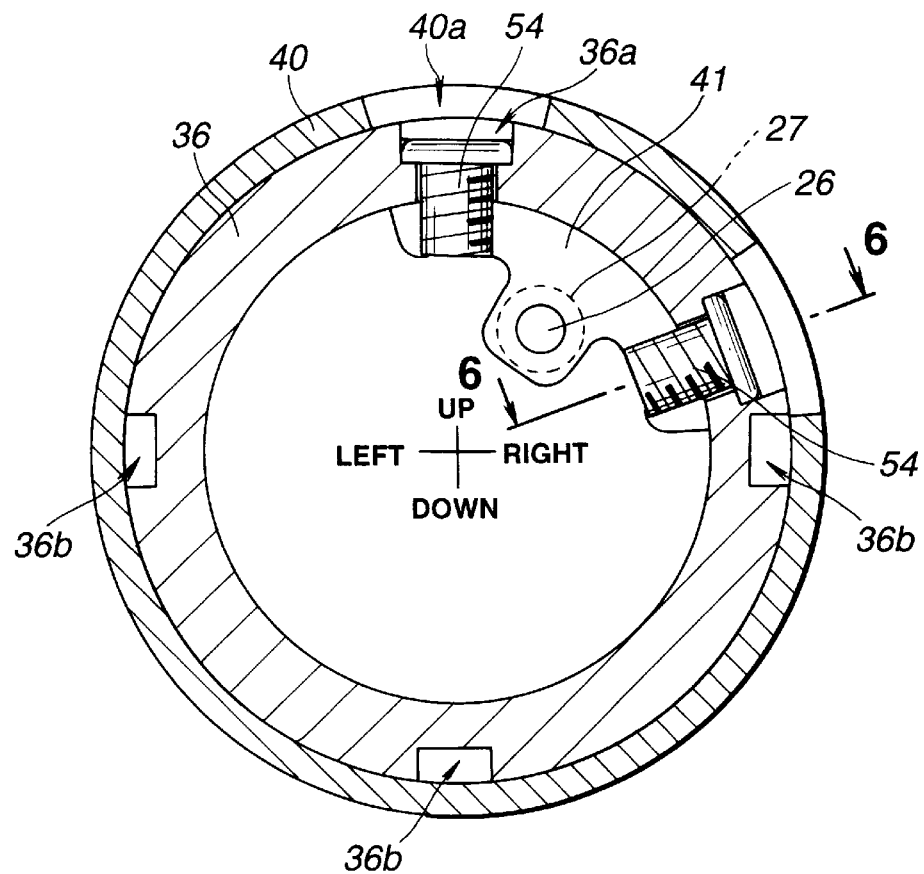

As shown in FIG. 5, the coil stopper 41 is fixed to the back-end base 36 by two screws 54 serving as a location changing means. A groove 36a cut in the back-end base 36 and an oblong hole 40a elongated in a longitudinal direction of the cylindrical tube 40 are located above each of the heads of the screws 54. This enables tightening or loosening of the screw 54 from the outside of the cylindrical tube 40.

A plurality of notches 36b is cut in the outer circumference of the back-end base 36 in order to produce a frictional resistance. The adoption of the notches 36b prevents the back-end base 36 and cylindrical tube 40 from shifting in directions of turning. Otherwise, the back-end base 36 and cylindrical tube 40 may shift in the directions of turning while they are being fastened by tightening the screw ring 39 after they are located at their ideal positions.

Figure 6:
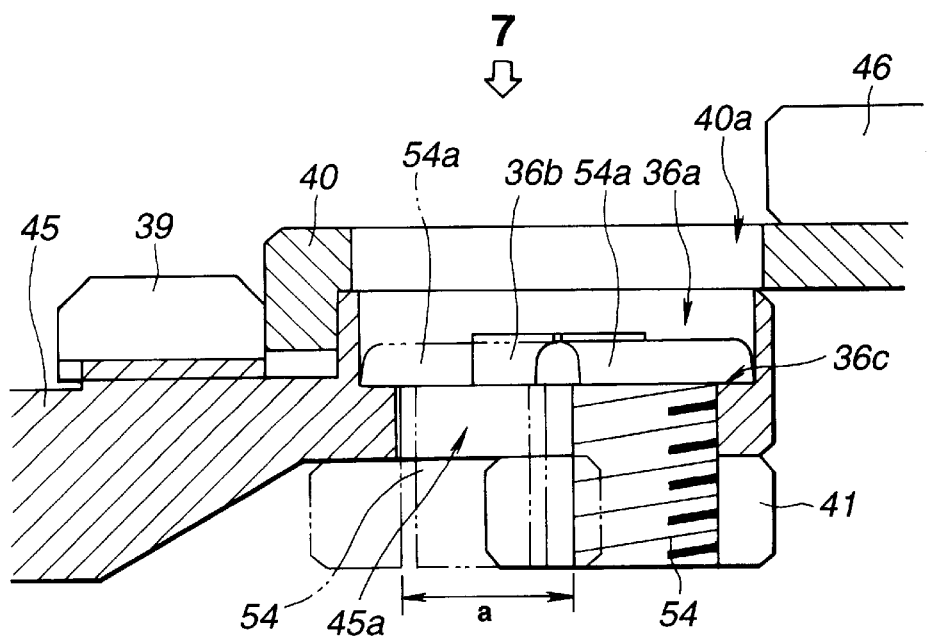

As shown in FIG. 6, oblong holes 45a elongated in a longitudinal direction are bored in the back-end base 36. This enables the screws 54 to slide by a distance a from the position indicated with a solid line to the position indicated with an alternate long and two short dashes line.

Figure 7:
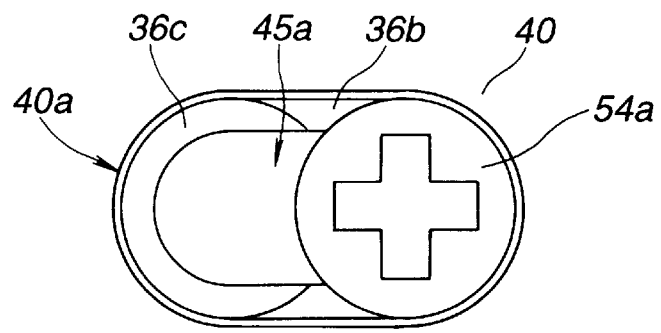

However, the grooves 36a of the back-end base 36 each have a step 36b. When the heads 54a of the screws 54 are, as shown in FIG. 7, placed on the bottoms 36c of the grooves 36a, the screws 54 cannot be slid in the direction indicated with an alternate long and two short dashes line. However, when the screws 54 are loosened until the heads 54a surmount the steps 36b, the screws 54 can slide within the oblong holes 45a and shift to the position indicated with the alternate long and two short dashes line.

The height of the steps 36b is set to be lower than the height at which the screws 54 stand when joined to the coil stopper 41. When the screws 54 are somewhat joined to the coil stopper 41, the heads 54a are floated. The screws 54 can now slide. The heads 54a can therefore be engaged with the front halves of the bottoms 36c shown in FIG. 7. When the screws 54 are tightened fully, they no longer slide due to the steps 36b. Furthermore, since the oblong holes 40a are bored in the cylindrical tube 40, the coil stopper 41 and the screws 54 can be shifted from the side of the outer circumference of the cylindrical tube 40.

In other words, the anti-breakage member 24 is peeled off from the support member 35. In this state, the filler 38 is extracted and the screws 37 are removed. This enables the support member 35 to slide towards the front end of the operation unit.

Figure 8:
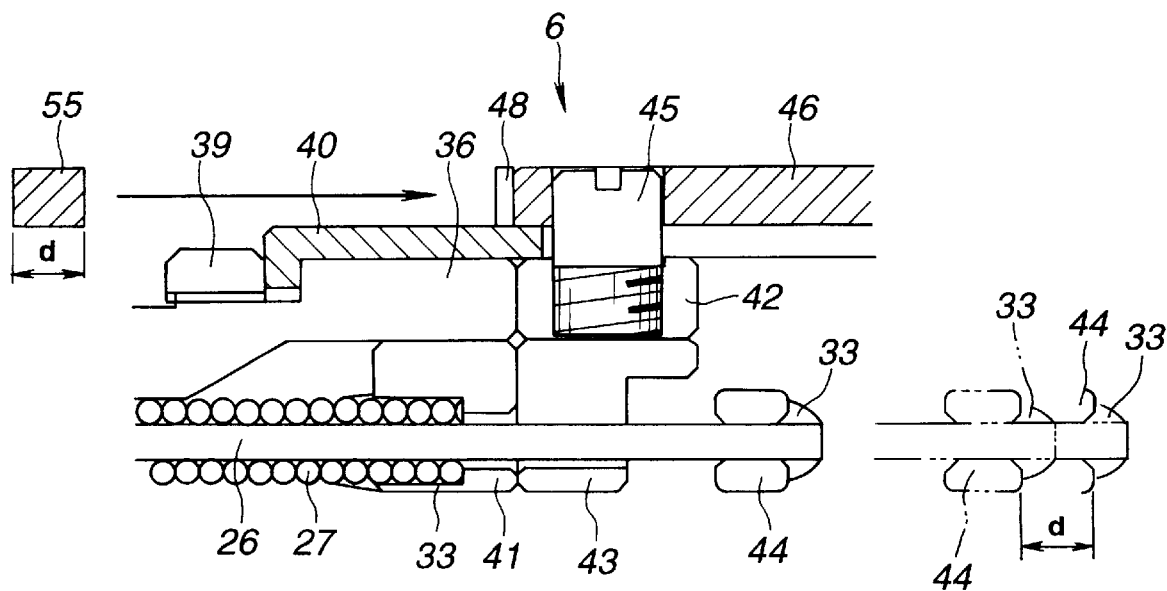

After the support member 35 is slid towards the front end of the operation unit, the hardness adjustment knob 25 can slide towards the front end thereof. FIG. 8 shows a state in which the anti-breakage member 24, support member 35, and hardness adjustment knob 25 are dismounted from the front end of the operation unit.

Figure 9:
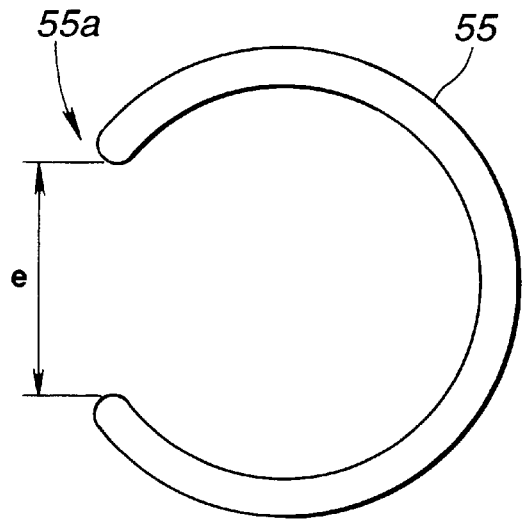

After the anti-breakage member 24, support member 35, and hardness adjustment knob 25 are dismounted from the front end of the operation unit, a spacer 55 is placed in front of the sliding ring 48. The spacer 55 having a thickness d is, as shown in FIG. 9, shaped substantially like the letter C so that it will fit on the outer circumference of the cylindrical tube 40.

With the spacer 55 placed, the dismounted support member 35 is fixed on the predetermined position of the back-end base 36 as previously. Consequently, the positions of the cam ring 46, movable pins 45, movable ring 42, and pull member 43 are changed backward from their initial positions by the thickness d of the spacer 55.

In this state, the hardness adjustment knob 25 and cam ring 46 are turned. This causes the movable pins 45, movable ring 42, and pull member 43 to move backward. However, the rearmost position of the wire stopper 44 also moves backward by the thickness d of the spacer 55 from its initial position indicated with an alternate long and two short dashes line. Accordingly, when the spacer 55 is made available in a plurality of kinds having different thicknesses d, the magnitude of movement can be adjusted properly.

The spacer 55 is shaped to have an inner diameter corresponding to the diameter of the cylindrical tube 40 on which the spacer 55 is fitted. The width of a notch 55a of the spacer 55 is made smaller than the outer diameter of the cylindrical tube 40 and larger than the outer diameter of the plastic tube 23. After the spacer 55 is fitted on the plastic tube 23 from a lateral direction, it can be placed in front of the sliding ring 48. For mounting the spacer 55, therefore, the anti-breakage member 24, support member 35, and hardness adjustment knob 25 need not be fully pulled out of the insertion unit 20. They may merely be shifted from the front end of the operation unit 6 to the middle of the plastic tube 23.

Moreover, the sliding ring 48 may operate as the spacer 55. Specifically, the sliding ring 48 is made available in a plurality of kinds having different widths. Any of the kinds of sliding rings is selected properly, whereby the same operation as that of the spacer 55 is provided.

In any case, the endoscope is structured to have a space permitting mounting of the spacer 55, thus providing a means for correcting the length of the distal part of a wire.

Figure 10:
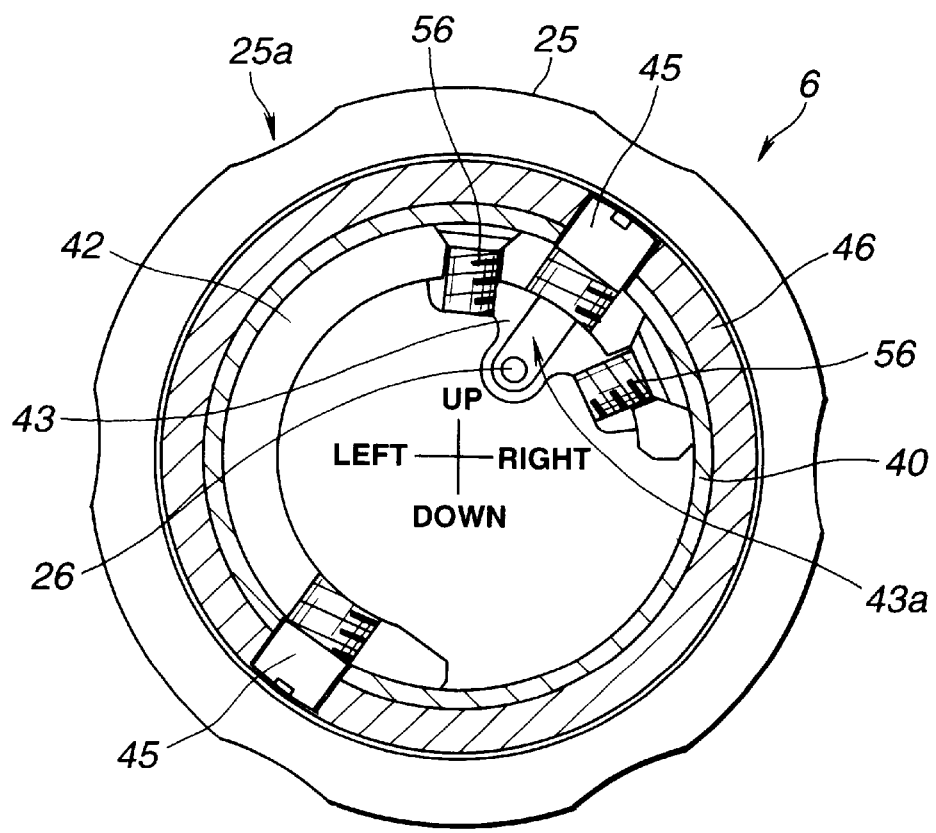

As shown in FIG. 10, the pull member 43 is fixed to the movable ring 42 by two screws 56. The pull member 43 has a groove 43a cut therein. The wire 26 can therefore be fitted on the outer circumference of the pull member 43 and then fixed to the movable ring 42.

The movable ring 42 is shaped like the letter C and has a space large enough for other contents to pass through it. Moreover, since the movable pins 45 are symmetrically arranged, the movable ring 42 is well balanced. Furthermore, the hardness adjustment knob 25 has a plurality of concave parts 25a as parts of the outer circumference thereof. The plurality of concave parts 25a prevents slippage of a hand gripping the hardness adjustment knob.

As shown in FIG. 11, pluralities of concave and convex parts formed on the inner circumference of the adjustment knob 25 and pluralities of concave and convex parts of the cam ring 46 are meshed with one another. The direction of turning is thus fixed. In this state, the hardness adjustment knob 25 and cam ring 46 can freely slide in directions along the longitudinal axis of the insertion unit. The cam ring 46 can be turned relative to the cylindrical tube 40.

Figure 12:
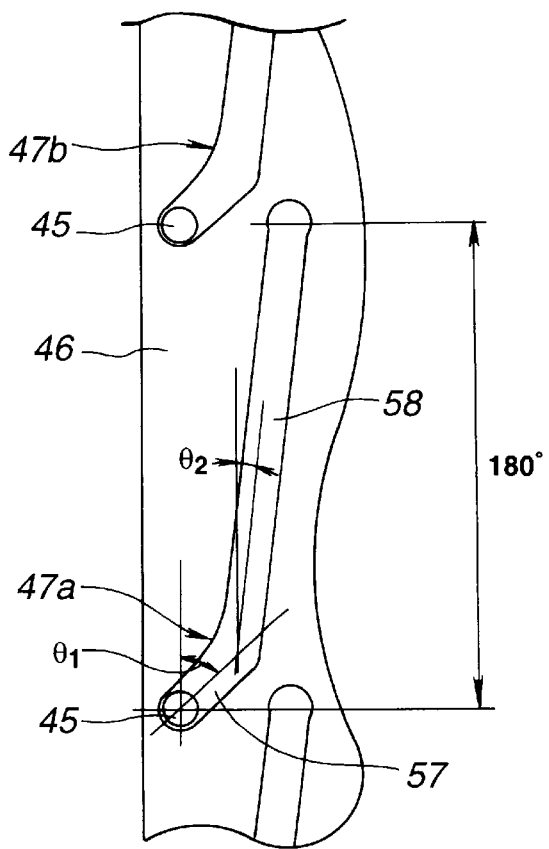

As shown in FIG. 12, the angle θ1 made by first travel sections 57 of cam grooves 47a and 47b is different from an angle θ2 made by second travel sections 58 thereof located toward the back of the first travel section. Assume that the cam ring 46 is turned and the movable pins 45 slide within the cam grooves 47a and 47b. In this case, a very large force is not required at first in order to pull the back end of the wire 26 relative to the coil 27. After the back end of the wire is pulled to some extent, the force required for pulling increases gradually.

Specifically, the movable pins 45 that move along the first travel sections 57 are pulled by a larger magnitude responsively to a small turn made by the cam ring 46. When the movable pins 45 have shifted to the second travel sections 58, a small magnitude of pull is attained with a large magnitude of turning. It is thus prevented that an operation force gets too large with a turn made by the cam ring 46.

If each cam groove did not have the travel sections but had the first travel section 57, which defines the angle θ1, from the beginning to the end, the magnitude of turning by which the cam ring 46 is moved would increase substantially. In the present invention, a maximum magnitude of turning (stroke) by which the cam ring 46 is moved is set to 180°, through which an operator can move the cam ring with one manipulation. The operation force is kept to a minimum. Alternatively, the maximum magnitude of turning may be set to any angle other than 180°.

Moreover, a gap serving as play is preserved between the pull member 43 and wire stopper 44. When the plastic tube 23 shown in FIG. 4 is softened, the plastic tube 23 bends. The back end of the wire 26 is pulled into the front-end part of the coil 27. At this time, the coil 27 will not be hardened. In other words, the plastic tube 23 is prevented from hardening naturally when the hardness adjustment knob 25 is not manipulated.

A description will be made of manipulations for changing the hardness of the plastic tube 23 from a soft level to a hard level.

First, the hardness adjustment knob 25 is turned in order to harden the plastic tube 23. This causes the cam ring 46 to turn together with the hardness adjustment knob 25. The movable pins 45 move long the cam grooves 47a and 47b, whereby the pull member 43 is moved backward. The pull member 43 thus moves backward to abut the wire stopper 44.

Thereafter, the pull member 43 further moves backward. The wire 26 is then pulled rearward. A compressing force is applied to coil 27, whereby the coil 27 is hardened. Thus, the hardness of the plastic tube 23 is changed from the soft level to the hard level.

A practical example of manipulations of the endoscope will be described with reference to FIG. 13A to FIG. 13C.

Figure 13A:
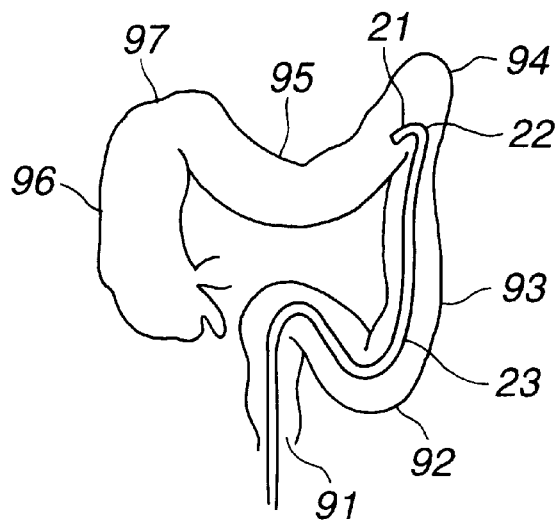
FIG. 13A to FIG. 13C are diagrams for explaining the practical operation of a hardness adjusting means incorporated in an endoscope.
Figure 13B:
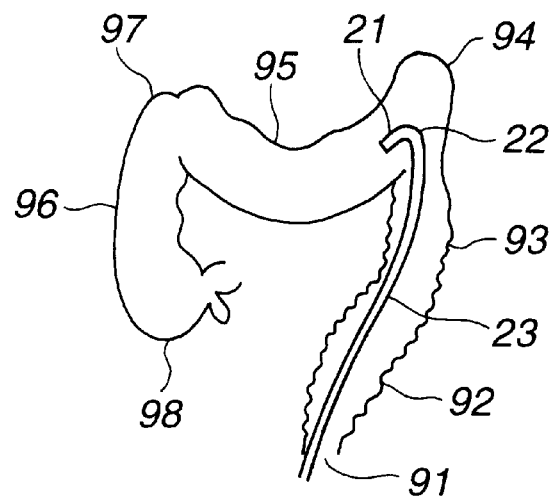
Figure 13C:
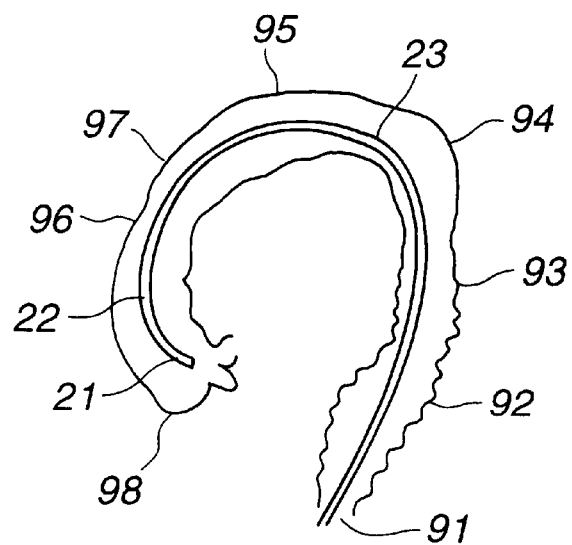

FIGS. 13A to 13C show scenes where the insertion unit 20 of the endoscope 2 is being inserted into the large colon.

As shown in FIG. 13A, the plastic tube 23 is softened, and the insertion unit 20 is passed into the anus 91, through the rectum, and inserted into the tortuous sigmoid colon 92. At this time, the plastic tube 23 is soft. Therefore, even if the middle of the plastic tube 23 is looped, a patient's discomfort can be suppressed. The distal part 21 of the insertion unit 20 then passes through the descending colon 93 and reaches near the curved portion 94.

The plastic tube 23 is, as shown in FIG. 13B, pulled in order to collapse the sigmoid colon 92. The plastic tube 23 and sigmoid colon 92 are straightened substantially linearly. The hardness adjustment knob 25 is then turned in order to harden the plastic tube 23. With the plastic tube hardened, the distal part 21 is advanced towards the transverse colon 95. This prevents the collapsed sigmoid colon 92 from bending and looping again.

As shown is FIG. 13C, the plastic tube 23 is hardened and the distal part 21 is advanced. The distal part 21 passes through the transverse colon 95, goes beyond the curved portion 97 of the liver, and reaches the cecum 98. The plastic tube 23 is rigid when hardened. This prevents the plastic tube 23 from looping again in the sigmoid colon 92. Moreover, the transverse colon 95 is prevented from bending to the greatest possible extent. The plastic tube can therefore be inserted smoothly. Besides, manipulations performed by an operator can be conveyed smoothly to the distal part. Consequently, insertion can be achieved smoothly.

However, as mentioned above, hardness adjustment is implemented for hardening the plastic tube 23 in the course of inserting the insertion unit 20 of endoscope 2 into an intended region. As the hardness adjustment is implemented frequently, the deterioration of the coil 27 and wire 26 will progress. In other words, when hardness adjustment is implemented frequently, the coil 27 contracts to shorten its natural length due to plastic deformation. By contrast, the wire 26 stretches to extend its natural length.

When the coil 27 and wire 26 deteriorate, the highest hardness attained when the plastic tube 23 is hardened decreases as mentioned above. Further, in this embodiment, when the wire 26 deteriorates and stretches, no load will be imposed on the flexible tube 14 in a longitudinal axial direction. However, when the coil 27 deteriorates, a load may be imposed thereon.

Specifically, the coil 27 contracts due to elastic deformation caused by pulling the wire 26. For this reason, the back end of the coil 27 is slightly pushed into the flexible tube 14 and slightly slacked therein in advance. In this state, the coil stopper 41 is fitted on the back-end base 36.

More particularly, assume that the plastic tube 23 apparently contracts about 2 mm due to elastic deformation when hardened most greatly. The back end of the coil 27 is pushed into the flexible tube 14 excessively by about 2 mm in comparison with its natural state. The back end thereof is then fitted into the back-end base 36. The linkage tube 13 is thus prevented to the greatest possible extent from being pulled when the plastic tube 23 is hardened most greatly.

If the linkage tube 13 were pulled, a force would work on the flexible tube 14 to contract it. This causes the flexible tube 14 to become twisted and deteriorate. Furthermore, the coil 27 may deteriorate and contract in natural length. In this case, when the wire 26 is pulled by manipulating the hardness adjustment knob 25, the linkage tube 13 may be pulled rearward beyond the position at which it stays before the coil 27 has deteriorated. A further load may be imposed on the flexible tube 14, thus affecting insertion smoothness or durability.

However, according to the present invention, the position of the back end of the coil 27 can be changed as shown in FIG. 6 and FIG. 7.

Specifically, when the coil 27 contracts due to deterioration, the screws 54 are loosened in order to change the position of the coil stopper 41. After the contraction of the coil 27 is thus corrected, the screws 54 are tightened. Consequently, it can be prevented that when the hardness adjustment knob 25 is manipulated, an excess load is imposed on the linkage tube 13. According to the structure of this embodiment, not only the deterioration of the coil 27 but also the deterioration of the wire 26 can be, as shown in FIG. 8, accommodated by the placement of the spacer 55 of a desired thickness.

Assume that numerous positions are defined as the positions at which the screws 54 are tightened in order to correct for a magnitude by which the coil 27 is pushed into the flexible tube 14. In practice, both the coil 27 and wire 26 deteriorate. Even if the magnitude by which the coil 27 is pushed in it initial state was reproduced, the greatest hardness of the coil attained in the initial state could not be regained.

By contrast, assume that the coil 27 is pushed inward until the greatest hardness attained in the initial state is regained. In this case, the coil 27 is pushed inward by a larger magnitude than the magnitude by which the coil is pushed inward in the initial state. Consequently, the linkage tube 13 stretches towards the front end of the plastic tube. An excess load is imposed on the flexible tube 14, whereby the flexible tube 14 is stretched.

As mentioned above, according to this embodiment, a magnitude by which the coil 27 is pushed into the flexible tube 14 is corrected for according to the deterioration of the coil 27 and wire 26. Moreover, the relative position of the wire 26 with respect to its position when the plastic tube is hardened most greatly is corrected according to the deterioration of the coil 27 and the wire 26. The initial state in which a small load is imposed on the flexible tube 14 and the initial state in which the plastic tube is hardened most greatly can thus be restored.

Supposing that what is corrected for at a certain time instant was only the magnitude by which the coil is pushed inward, an ideal load might not be imposed on the flexible tube at that time. However, the coil or wire may deteriorate again during the subsequent use. In this case, the wire alone should be corrected to account for the deterioration. Thus, the correction would be achieved not to impose an excess load on the flexible tube. Moreover, assume that the wire alone is corrected previously. In this case, an excess load may be imposed on the flexible tube with the plastic tube at its greatest hardness. However, the coil alone should be corrected thereafter. It can thus be prevented that an excess load is imposed on the flexible tube. Thus, the coil and wire advantageously can be correctly respectively.

Using FIG. 2, FIG. 4, and FIG. 5 that have been referred to previously, a description will be made of a location changing means different from one in the embodiment. The location changing means determines the position of the back end of the coil 27.

As shown in FIG. 2, the distal end of the coil 27 is fixed to the distal part of the wire 26. Moreover, the distal part of the wire 26 is locked in the linkage tube 13. The distal end of the coil 27 may be twisted a little on an elastic deformation basis. However, the distal end of the coil 27 will hardly be turned in its natural state.

On the other hand, the back end of the coil 27 is locked in the coil stopper 41 so that the coil 27 will not be turned. The coil stopper 41 is, as shown in FIG. 5, fixed to the back-end base 36 so that it will not be turned.

However, when the two screws 54 are fully removed from the coil stopper 41, the coil stopper 41 can be turned relative to the back-end base 36 within the internal space of the back-end base 36.

When the coil stopper 41 is turned, the back end of the coil 27 turns. When the back end of the coil 27 is turned, the front end of the coil 27 does not turn very much because of the restrictions on the front end of the wire 26. Specifically when the coil stopper 41 is turned, the pitch of the coil 27 varies, that is, the number of turns of the coil 27 changes. If the number of turns can be changed, it means that the overall length of the coil 27 can be changed proportionally to the diameter of a wire wound as a coil.

As mentioned above, when the coil 27 deteriorates and contracts, the coil stopper 41 is turned, for example, once or a plurality of times in a direction in which the overall length of the coil 27 extends. Thereafter, the coil stopper 41 is fixed again to the back-end base 36 using the screws 54. The coil 27 can thus be corrected for the natural length so that the natural length will be substantially identical to that attained in the initial state. Correcting for the natural length can be achieved in units of the diameter of the wire of the coil 27. This results in high-precision and considerably refined correction.

Moreover, because a load imposed on the flexible tube 14 by the hardness adjusting means can be adjusted, the length of the hardness adjusting means can be adjusted (corrected)

according to a difference in length of the flexible tube 14 at a step in the manufacturing process. Thereafter, assembling can be carried out. Consequently, an endoscope offering good initial quality can be delivered.

Referring to FIG. 14 to FIG. 19, the second embodiment of the present invention will be described below.

In this embodiment, the coil and wire included in the hardness adjustment means can be replaced with new ones.

A brief description initially will be made of a hardness adjusting means of this embodiment for adjusting the hardness (plasticity) of the plastic tube 23 of the insertion unit 20.

In this embodiment, the aforesaid coil and wire are integrated into a hardness adjustment unit. A unit mounting means is included for enabling mounting and dismounting of the distal and back-end members of the hardness adjustment unit in and from an endoscope. In short, the hardness adjustment unit can be mounted near the front end and back end of the plastic tube 23 of the endoscope 2.

Figure 14A:
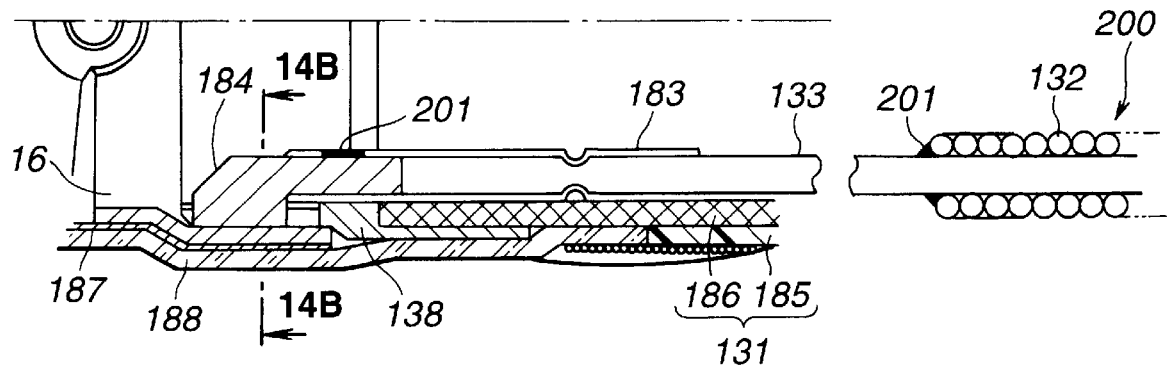
FIG. 14A to FIG. 14D are diagrams showing the structures of the linkage member linking a bendable part and plastic tube and its surroundings.
Figure 15:
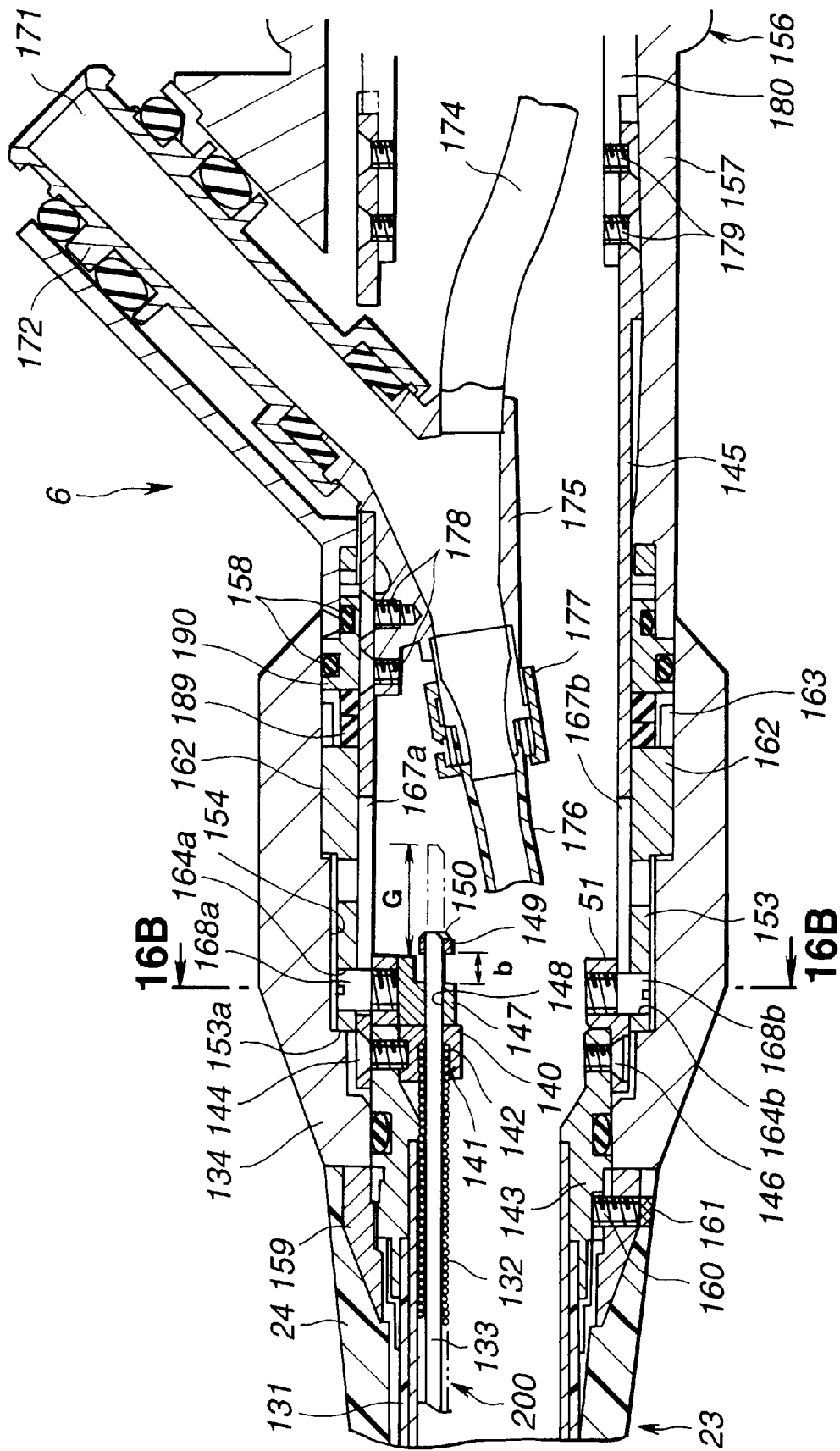

As shown in FIG. 14A and FIG. 15, a hardness adjustment unit 200 composed of a metallic coil 132 and a plastic wire 133 is passed through a flexible tube 131 serving as armor of the plastic tube 23. The metallic coil 132 has a wire wound densely in the form of an elongated pipe, and the plastic wire 133 is passed through the coil 132. The metallic coil 132 and plastic wire 133 constitute a hardness adjusting means.

Figure 14B:
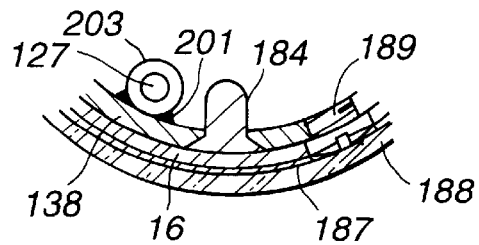

The distal end of the coil 132 and the distal end of the plastic wire 133 are fixed to the inner circumference of a linkage tube 138 via a linkage member 184 shown in FIG. 14A and FIG. 14B. The linkage member 184 will be described later. Alternatively, the distal part of the wire 133 may be attached and fixed near the distal end of the coil 132 locked in the linkage tube 138. The distal end of the wire 133 may be attached to the linkage tube 138. The distal end of the coil 132 may then be fixed to the middle of the wire 133 located slightly behind the distal end of the wire attached to the linkage tube by performing brazing or the like. The attachment and fixation are not limited to any specific method.

The distal part of the hardness adjustment unit 200 including the coil 132 and wire 133 is attached to the linkage tube 138. Thus, the coil 132 and wire 133 are prevented from being entangled with the other components to thus injure them.

When the linkage tube 138 is uncoupled from the back-end joint section 16 that is an integral part of the bendable part 22, the distal part of the wire 133 can be unlocked from the linkage tube 138.

As shown in FIG. 15, the operation unit 6 has an adjustment manipulating means to be manipulated for adjusting the hardness of the hardness adjustment unit.

The adjustment manipulating means is a cylindrical hardness adjustment knob 134 serving as an adjusting mechanism to be manipulated for hardness adjustment. The hardness adjustment knob 134 is provided as, for example, the front-end region of the operation unit 6 adjoining the anti-breakage member 24. The states of the coil 132 and wire 133 constituting the hardness adjusting means are varied by turning the hardness adjustment knob 134. The hardness adjusting means is placed in the plastic tube 23. Finger rest grooves 136 (see FIG. 16B) are cut in the outer circumference of the hardness adjustment knob 134.

To begin with, a description will be made of the practical structure of the adjusting mechanism to be manipulated for hardness adjustment.

The proximal end of the coil 132 is locked in a member of a coil stopper 140 located in the front-end part of the operation unit 6. In other words, the proximal end of the coil 132 is locked in a hole 141 bored in the coil stopper 140. With the proximal end thereof abutted on the end surface of a front-end stepped bore 142 within the hole 141, a brazing filler such as solder or an adhesive is poured into the stepped bore 142.

The back end of the coil 132 is thus locked in the member of the coil stopper 140. Consequently, the back end of the coil 132 is restricted in its rearward movement beyond the position where the back end thereof is locked, and its turning restricted. Moreover, the coil 132 is locked in such a manner that it will not turn about the axis of the insertion unit 20.

On the other hand, the wire 133 lying through the coil 132 is passed through the hole 141 of the coil stopper 140 and extends rearward. The wire 133 can freely move back and forth relative to the coil 132.

The coil stopper 140 is fixed to a back-end base 43 for securing the back end of the flexible tube 131 to the operation unit 6, thus realizing a back-end unit part mounting means. The coil stopper 140 can be therefore be dismounted from the back-end base 143 by removing screws 144. The back-end base 143 is fixed to near the front end of a cylindrical tube 146 placed on the outer circumference of the back-end base 143 by means of the screws 144 and screws 146.

The proximal end of the wire 133, that is, the back end thereof is inserted into a linkage hole 148 bored in a pull member 147 so that the proximal end of the wire 133 can move freely. The proximal end thereof is firmly fixed to a stopper 149 separated by a gap b from the pull member 147 by performing brazing 150. The pull member 147 is slid rearward by a length corresponding to the gap b. The pull member 147 can thus be moved rearward together with the wire 133 and stopper 149.

Figure 16A:
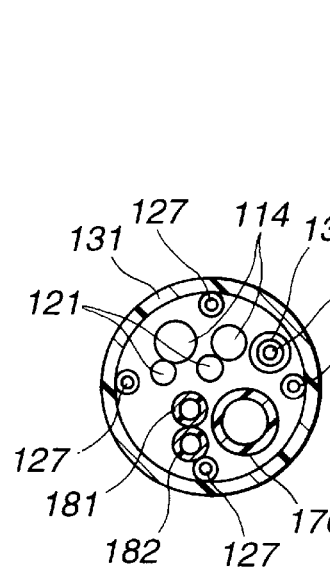
FIG. 16A and FIG. 16B are lateral sectional views showing the contents of an endoscope.
Figure 16B:
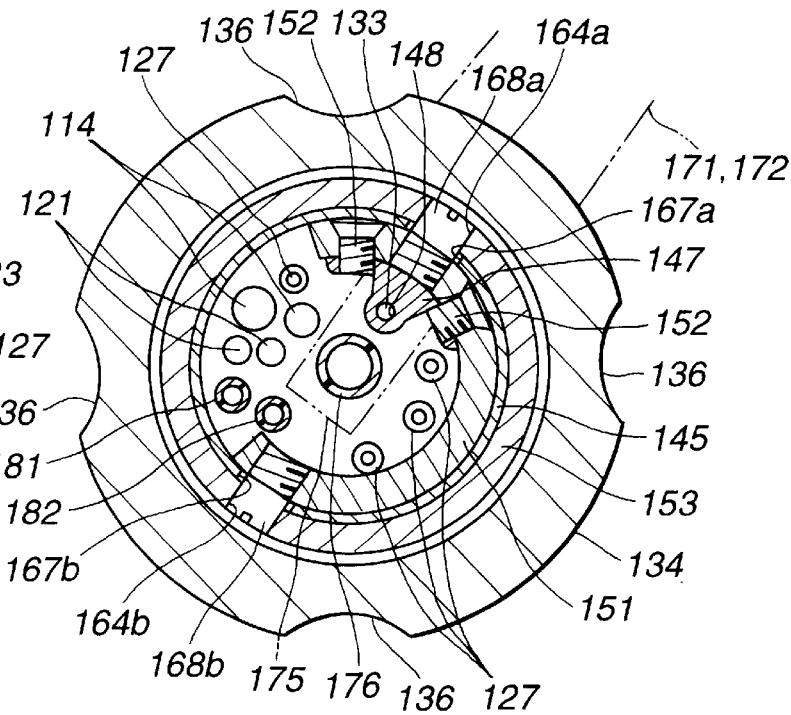

As shown in FIG. 16B, the pull member 147 abuts the inner circumference of a movable ring 151 that is a partly-notched cylindrical ring member, and fixed to the movable ring 151 by screws 152. The pull member 147 can therefore be dismounted from the movable ring 151 by removing the screws 152.

The outer circumference of the movable ring 151 is matched with the inner surface of the cylindrical tube 145 of the operation unit 6, and fitted thereon in close contact therewith. The movable ring 151 is thus permitted to move back and forth.

In other words, a guide means is thus realized for causing the movable ring 151 to move linearly back and forth. The pull member 147 can be moved back and forth together with the movable ring 151.

A cam cylinder 153 is mounted on the outer circumference of the cylindrical tube 145 so that the cam cylinder 153 can be turned freely. The cam cylinder 153 is locked in a stepped hole 154 cut in the inner surface of the hardness adjustment knob 134. The front end of the cam cylinder 153 abuts on the front end of the stepped hole 154, thus having advancement thereof restricted.

Moreover, the back end of the cam cylinder 153 abuts on a seal ring 190 mounted on the cylindrical tube 145, thus having withdrawal thereof restricted. The cam cylinder 153 is supported by the seal ring 190 via a plurality of C-shaped rings 189.

Figure 17:
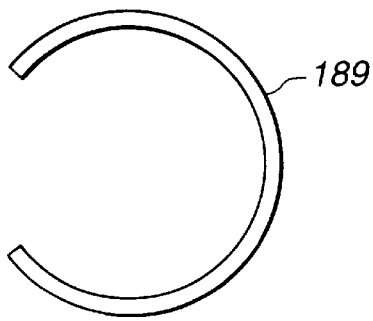

The width of the openings of the C-shaped rings 189 is larger than the outer diameter of the flexible tube 131 but smaller than the outer diameter of the cylindrical tube 145. FIG. 17 shows the shape of the C-shaped rings 189.

The seal ring 190 is positioned so that it cannot withdraw. The seal ring 190 is locked while abutting the front end of a cylindrical body 157 forming a grip portion 156 of the operation unit 6. The front half of the seal ring 190 is engaged with the inner surface of the back-end part of the hardness adjustment knob 134. In contrast, the back half of the seal ring 190 is engaged with the inner surface of the front-end part of the cylindrical body 157.

A seal member 158 such as an O ring is interposed between the outer circumference of the front half of the seal ring 190 and the hardness adjustment knob 134, and between the outer circumference of the back half of the seal ring 150 and the cylindrical body 157.

The front end of the hardness adjustment knob 134 abuts the back end of an annular bearing member 159 for bearing the anti-breakage member 24, whereby the forward movement of the hardness adjustment knob is restricted. The bearing member 159 is screwed to and engaged with the back-end base 143. The bearing member 159 is fastened to the back-end base 143 by means of a screw 160, whereby turning thereof is prevented. A hole into which the screw 160 is fitted is sealed with a filler 161.

The hardness adjustment knob 134 is mounted on the outer circumference of the cylindrical tube 145 via the cam cylinder 153. As mentioned above, the cam cylinder 153 is in contact with the outer circumference of the cylindrical tube 145 so that the cam cylinder 153 can be turned freely over the cylindrical tube 145. In this state, back-and-forth movement is restricted.

A plurality of locking bosses (convex parts) 162 are partly formed on the outer circumference of the cam cylinder 153. The bosses 162 are fitted into grooves (concave parts) 163 cut in the inner surface of the hardness adjustment knob 134. Since the bosses 162 are fitted into the grooves 163, the cam cylinder 153 and hardness adjustment knob 134 are coupled mutually so that they cannot be turned, though they are mutually separate. The cam cylinder 153 is turned in conjunction with the hardness adjustment knob 134.

Figure 18A:
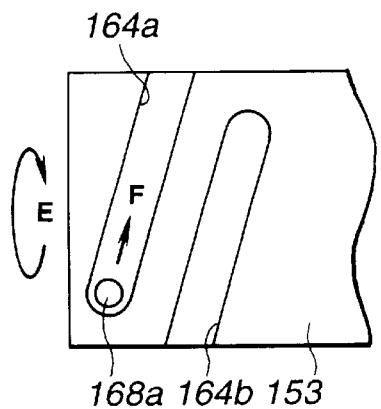
FIG. 18A and 18B are diagrams showing cam grooves.
Figure 18B:
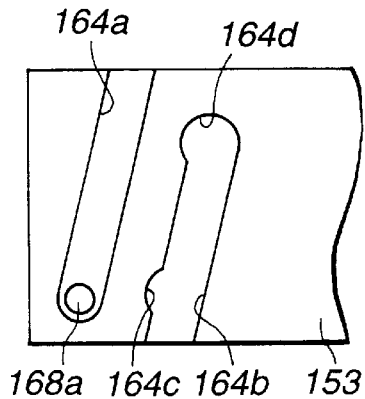

Two cam grooves 164a and 164b are cut spirally in the cam cylinder 153 in such a manner that they are opposed to each other and facing in the same direction with the same pitch maintained. FIG. 18A shows the shape of the cam grooves 164a and 164b in the cam cylinder 153.

The cam grooves 164a and 164b are cam grooves cut in a double-streak cam. The cam grooves 164a and 164b have the same shape. The cam grooves are cut to be opposed to each other with respect to the axis of the cam cylinder 153. When the cam cylinder is turned 180°, their positions are reversed.

In FIG. 18A, the cam grooves 164a and 164b are shaped like simple smooth grooves having a smooth spiral shape. The structure shown in FIG. 18B may be substituted for the structure shown in FIG. 18A. Specifically, a concave part 64c may be formed in the middle of a groove 64b, and a concave part 64d may be formed at the ends of the groove 64b. When pins 66a and 66b that will be described later are entrapped in the concave parts, an operator will sense a click.

Moreover, oblong holes 167a and 167b are, as shown in FIG. 15, bored in the cylindrical tube 145 so that the oblong holes 167a and 167b will be mutually opposed. The oblong holes 167a and 167b are elongated along the center axis of turning of the hardness adjustment knob 134. Two pins 168a and 168b are screwed to the movable ring 151. The pins 168a and 168b are fitted into the associated oblong hole 167a or 167b and the associated cam groove 164a or 164b.

The length of the oblong holes 167a and 167b is a length permitting coverage of a range within which the back end of the wire 133 should be moved (area G in FIG. 15). Herein, the length of the oblong holes 167a and 167b is a length between the front and back ends of the oblong holes 167a and 167b along the center axes thereof. Moreover, the length of the cam grooves 164a and 164b, which are cut in the cam cylinder 153, along the center axes thereof is larger than the length of the oblong holes 167a and 167b.

When turned, the hardness adjustment knob 134 causes the pins 168a and 168b to move forward or rearward within the oblong holes 167a and 167b along the cam grooves 164a and 164b in the cam cylinder 153. This causes the pull member 147 to move forward or rearward. When the pull member 147 abuts the stopper 149, the wire 133 lying through the coil 132 is advanced or withdrawn. Thus, an adjusting mechanism is realized.

Assume that the hardness adjustment knob 134 is turned in a direction E in FIG. 18A (the left side of FIG. 18A is the side of the insertion unit). In this case, the pin 168a moves, as shown in FIG. 18A, in the direction of arrow F along the cam groove 164a in the cam cylinder 153. Moreover, the pin 168a is passed through the oblong hole 167a elongated in a longitudinal direction of the cylindrical tube 145. The movable ring 151 therefore moves rearward along the oblong hole 167a with the pin 168a. Specifically, the pin 168a moves in a horizontal direction (rightward) in FIG. 18A in practice.

With the movement, the pull member 147 firmly screwed to the movable ring 151 moves rearward. When the pull member 147 moves by a distance d from the position indicated with a solid line in FIG. 15, the pull member 147 abuts the stopper 149.

Moreover, a force exerted by withdrawing the pull member 147 and stopper 149 is applied as a compressing force to the coil 132. This enables adjustment of varying the hardness of the coil 132.

To begin with, assume that the pull member 147 is not moved rearward. In this case, the pull member 147 abuts the coil stopper 140. The coil 132 having rearward movement restricted exhibits the greatest plasticity, that is, the lowest hardness. The coil 132 is therefore most readily bendable (softest).

When the pull member 147 moves rearward, it abuts the stopper 149. This causes the back end of the wire 133 to move rearward. Consequently, the coil stopper 140 exerts the operation of compression to push the coil 132 relatively forward.

Specifically, when a force is applied for causing the back end of the wire 133 to move rearward, a compressing force is applied to the coil 132. With the compressing force, the plasticity of the coil 132 that is elastic is lowered, that is, the hardness thereof is raised. The coil 132 therefore becomes so hard as not to be bent readily (or more particularly, hard enough to resist being bent).

In this case, the magnitude of the compressing force to be applied to the coil 132 can be varied depending on the magnitude of the rearward movement made by the pull member 147. In other words, the hardness (plasticity) of the coil 132 can be varied. Thus, a hardness adjusting means is realized.

On the other hand, the operation unit 6 shown in FIG. 15 has an insertion port frame 172, which defines a treatment appliance insertion port 171, located at a forward position and adjoining the grip portion 156. The insertion port frame 172 is linked to a bifurcation member 175 bifurcating in the operation unit 6 into a channel reaching the treatment appliance insertion port 171 and a suction channel 174. The proximal end of a treatment channel tube 176 lying through the insertion unit 20 is linked to the front end of the bifurcation member 175 by means of a linkage unit 177.

The bifurcation member 175 is fixed to the cylindrical tube 145 by means of screws 178. The cylindrical tube 145 has its back end coupled to a frame body 180 by screws 179. An angling manipulation mechanism of the operation unit 6 is mounted on the frame body 180. The cylindrical tube 145 is mounted so as not to turn despite a turn of the hardness adjustment knob 134.

Various devices like the ones shown in FIG. 16A are arranged in the insertion unit 2. Specifically, contained are four angling wires 127, two signal lines 121, two light guides 114, a treatment appliance channel tube 176, the coil 132 and wire 133, an aeration tube 181, and a perfusion tube 182. The four angling wires 127 are arranged up and down, and right and left. The two signal lines 121 are arranged near the center of the insertion unit 2. The two light guides 114 are arranged in an upper central area. The treatment appliance channel tube 176 is located at a lower position. The coil 132 and wire 133 are located at an upper right position. The aeration tube 181 used for aeration is located at a lower left position. The perfusion tube 182 used for perfusion is located below the aeration tube 181. Moreover, the contents shown in FIG. 16B are arranged in the operation unit 6. The arrangement of the contents of the operation unit 6 becomes slightly different from the one shown in FIG. 16A near the bifurcation member 175.

Figure 14C:
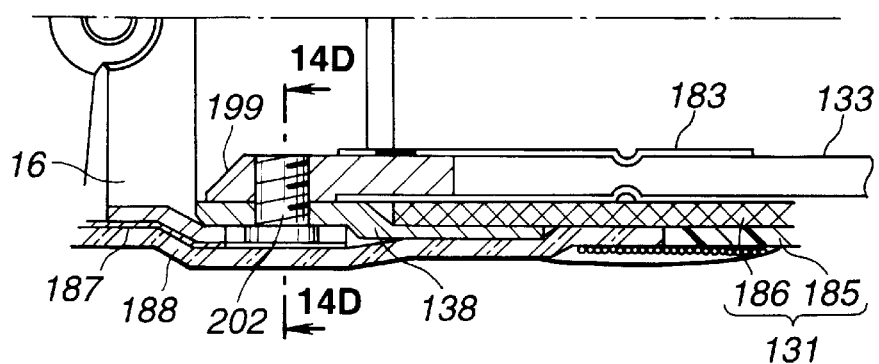
Figure 14D:
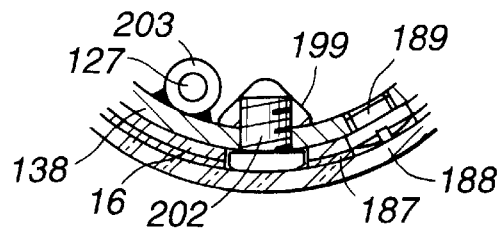

Now, a description will be made of a hardness adjustment unit, which is constituent feature of this embodiment, with reference to FIG. 14A and FIG. 14D.

As shown in FIG. 14A, the distal end of the coil 132 that is an integral member of the hardness adjustment unit 200 is firmly fixed to the middle of the wire 133 using a brazing filler 201 or the like.

Moreover, the linkage member 184 is partly fitted into the linkage pipe 183 and firmly secured by the brazing filler 201 or the like. The distal end of the wire 133 is inserted into the linkage pipe 183 until it abuts the linkage member 184. The distal end of the wire 133 is partly caulked, thus being secured firmly.

The caulked portion of the wire 133 and its surroundings may be bonded to the linkage pipe 183 using an adhesive for further increasing the fixation strength. Needless to say, the linkage member 184 and linkage pipe 183 may be machined as a single piece.

As mentioned above, the linkage member 184, linkage pipe 183, wire 133, coil 132, coil stopper 140, pull member 147, and stopper 149 are integrated into the one hardness adjustment unit 200.

The linkage member 184 serving as the distal part of the hardness adjustment unit 200 is, as shown in FIG. 14B, slid and fitted into the distal part of the linkage tube 138. The linkage member 184 has a flange so as not to slide into the linkage tube 138. Part of the back-end joint section 16 is mounted on the linkage tube 138 and secured by a screw 202.

As mentioned above, the back-end joint section 16 is fixed to the linkage tube 138. The linkage member 184 is therefore positioned and coupled firmly to the linkage tube 138. The back-end joint section 16 is separated from the linkage tube 138 by loosening and removing the screw 202. The linkage member 184 serving as the distal part of the hardness adjustment unit 200 can thus be uncoupled from the linkage tube 138. These are the operations of a distal unit part mounting means.

Incidentally, the flexible tube 131 covering the plastic tube 23 is composed of a metallic tube 186 and an armor 185 overlying the metallic tube. Moreover, the back-end joint section 16 that is an integral part of the bendable part 22 is covered with a mesh tube 187 and a rubber armor 188. The back end of the rubber armor 188 and the armor 185 are spliced firmly using a bobbin and adhesive.

The mounting means positions the distal part of the hardness adjustment unit 200 and couples it firmly to the linkage tube 138. The mounting means may be realized by utilizing the screw 202 as shown in FIG. 14C and FIG. 14D. That is to say, a linkage member 199 is coupled firmly to the linkage tube 138 by the screw 202.

In either of the unit mounting means, if only the back-end joint section 16 is disconnected from the linkage tube 138, the linkage member 184 (or linkage member 199 shown in FIG. 14C and FIG. 14D) can be uncoupled readily from the linkage tube 138. A coil pipe 203 enclosing the angling wires 127 is located near the position at which the linkage member 184 is coupled to the linkage tube 183. The coil pipe 203 is fixed firmly to the linkage tube 138 using the brazing filler 201 or the like so that it will not come off.

Moreover, the distal linkage member of the hardness adjusting means and the back-end linkage member thereof are fully incorporated in the endoscope 2 to prevent an operator from uncoupling them. This is intended to prevent the operator or any other person from modifying the quality unintentionally.

Assume that the function of varying the hardness (plasticity) of the plastic tube 23 is used repeatedly during an examination like the one shown in FIG. 13A to FIG. 13C. In this case, the coil 132 may contract gradually due to plastic deformation or the wire 133 may stretch gradually due to plastic deformation. The function may therefore deteriorate (the plastic tube 23 may not be hardened as greatly as it was initially). Referring to FIG. 15, the gap b attained with the plastic tube in its most softened state may get wider. In this case, replacement and repair is carried out as described below.

To begin with, the screw 160 is removed from the back-end base 143. The bearing member 159 and an anti-breakage tube 110 are dismounted from the back-end base 143 (or slid forward over the flexible tube 131).

Thereafter, the hardness adjustment knob 134 is dismounted (or shifted) forward. The pins 168a and 168b are removed from the movable ring 151 and cam cylinder 153.

The cam cylinder 153 is then dismounted from the cylindrical tube 145 (or shifted forward in the plastic tube 23).

Herein, one or two of the C-shaped rings 189 are shifted forward and dismounted from the cylindrical tube 145. The C-shaped rings 189 can be dismounted sideways from the flexible tube 131. This is because the openings of the C-shaped rings 189 are larger than the outer diameter of the flexible tube 131.

After one or two C-shaped rings 189 are dismounted from the flexible tube 131, the cam cylinder 153 is remounted on the cylindrical tube 145. The pins 168a and 168b are fixed again to the movable ring 151 through the cam grooves 164a and 164b. The dismounted C-shaped rings 189 are fitted on the flexible tube 131 from the flank of the flexible tube 131, and remounted on the cylindrical tube 145. The C-shaped rings 189 then abut the front end 153a of the cam cylinder 153.

The hardness adjustment knob 134, bearing member 159, anti-breakage tube 110, and screw 160 are then returned in place. Consequently, the positions of the hardness adjustment knob 134 and bearing member 159 are unchanged from the previous ones. However, the C-shaped rings 189 are now interposed between the front end 153a of the cam cylinder 153 and the hardness adjustment knob 134. Thus, when the plastic tube is softened, the cam cylinder 153 is located farther rearward by the width of the C-shaped rings 189.

In other words, assume that the wire 133 has stretched relative to the coil 132 (plastic deformation). When the plastic tube is softened, the coil stopper 140 and pull member 147 are spaced from each other. The space is compensated for using the C-shaped rings 189. The C-shaped rings 189 work as a spacer.

As another adjusting method, it is conceivable to, for example, place the spacer directly between the pull member 147 and stopper 149. However, in this case, the cylindrical tube 145 must also be dismounted from the back-end base 143 toward the flexible tube 131. Various contents for the cylindrical tube 145 must be displaced for the work.

As mentioned above, when the cylindrical tube 145 is dismounted towards the flexible tube 131, the cylindrical tube 145 must be uncoupled from the frame body 180. The insertion port frame 172 must be detached from the bifurcation member 175. Additionally, the bifurcation member 175 must be freed from the cylindrical tube 145. This work is rather time-consuming.

According to this embodiment, the relative position of the coil 132 and wire 133 in the back-end base 143 and the relative position thereof in the cylindrical tube 145 can be corrected outside the back-end base 143 and cylindrical tube 145 enclosing the components. Herein, the relative positions can be attained with the plastic tube in a hardened state. The work is comparatively easy to do. Moreover, there is no fear that the other components will be injured.

Any other method may be adopted to correct the relative position of the coil 132 and wire 133 to be attained with the plastic tube in a hardened state. Whatever method is adopted, correction should be able to be achieved outside the back-end base 143 and cylindrical tube 145.

Assume that the plastic tube 23 is driven forcefully while hardened, though it may rarely occur. The coil 132 may be buckled or the wire 133 may be broken. The linkage member 184 and linkage tube 138 may be uncoupled from each other. The linkage pipe 183 and linkage member 184, the linkage pipe 183 and wire 133, the coil 132 and wire 133, the wire 133 and coil stopper 140, or the wire and brazing filler 201 may conceivably be freed from each other.

Moreover, the magnitude by which the aforesaid coil 132 and wire 133 are plastically deformed may become too large to be withstood using the C-shaped rings 189. In this case, according to this embodiment, the hardness adjustment unit 200 may be freed from the insertion unit 20 and operation unit 6 of the endoscope 2. A new hardness adjustment unit 200a may then be substituted for the hardness adjustment unit 200. Incidentally, the hardness adjustment unit 200 includes the coil 132 and wire 133, or more particularly, consists of the linkage member 184, linkage pipe 183, wire 133, coil 132, coil stopper 140, pull member 147, and stopper 149.

Referring to FIG. 19A to FIG. 19D, the replacement procedure will be described in detail.

Figure 19A:
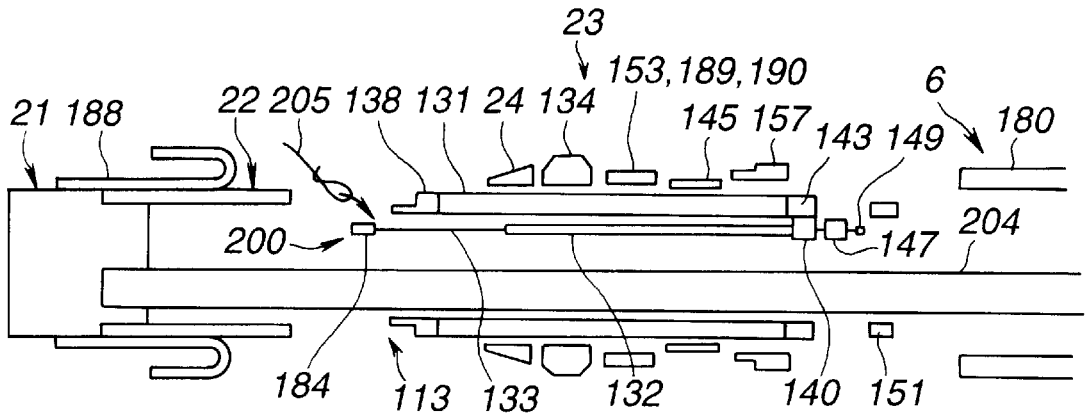
FIGS. 19A to 19D illustratively show a procedure of replacing a hardness adjustment unit with a new one.
Figure 19B:
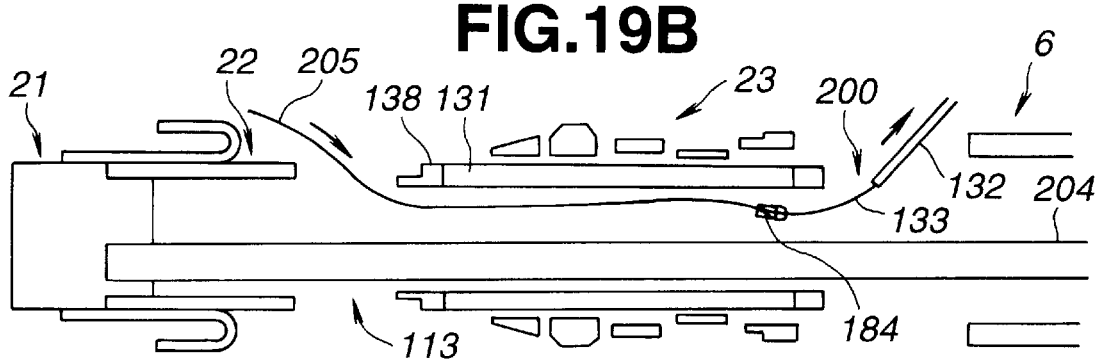
Figure 19C:
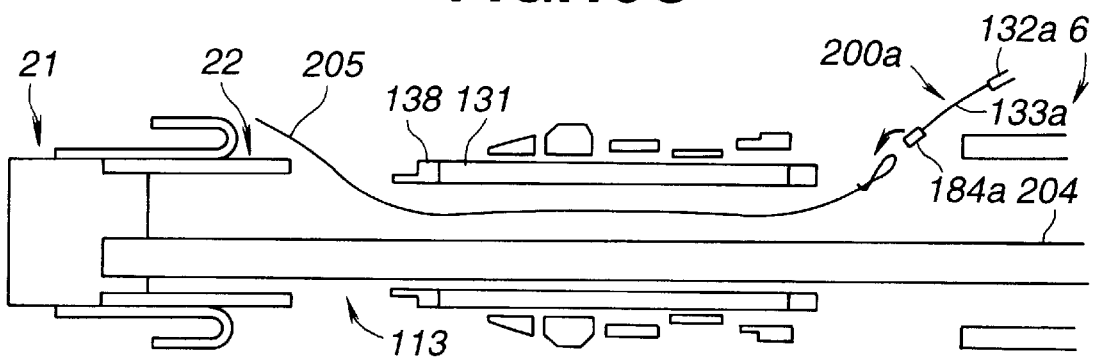
Figure 19D:
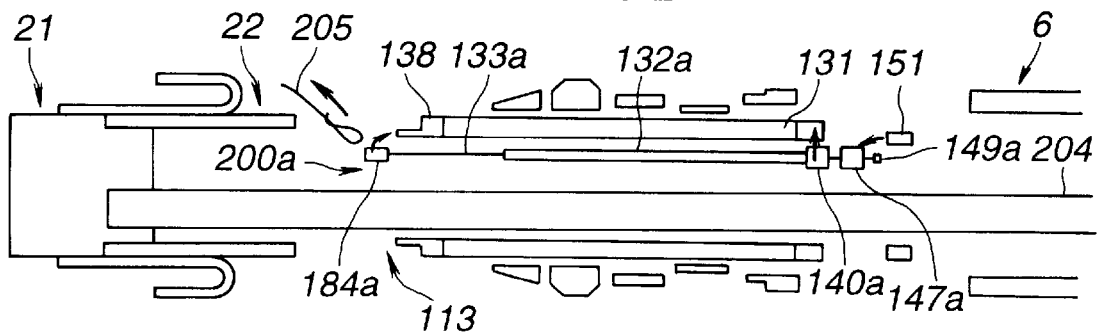

FIG. 19A to FIG. 19D illustratively show the structure of the endoscope 2. The shown components are considerably different in size and shape from the actual ones. For convenience, the reference numerals are assigned to the components shown in FIG. 19A alone. In FIG. 19B, FIG. 19C, and FIG. 19D, only major members bear the reference numerals.

First, the back end of the rubber armor 188 in the distal part of the endoscope 2 is detached from the flexible tube 131 and peeled back.

Thereafter, the back end of the bendable part 22 is freed from the linkage tube 138. Note that the various components of the insertion unit 20 shall be collectively referred to as component 204. The component 204 somewhat slackens in the insertion unit 20 or operation unit 6. The distal part 21 is pulled, whereby some space 113 can, as shown in FIG. 19A, be created between the distal end of the linkage tube 138 and the back end of the bendable part 22.

On the other hand, the anti-breakage member 110 of the operation unit 6 is freed from the back-end base 143. The hardness adjustment knob 134 is shifted forward. The pins 168a and 168b are removed from the movable ring 151. The cam cylinder 153, C-shaped rings 189, and seal ring 190 are orderly shifted forward over the flexible tube 131. The insertion port frame 172 is uncoupled from the bifurcation member 175. The cylindrical tube 145 is then freed from the back-end base 143 and frame body 180, and shifted forward up to the cylindrical body 157.

A string 205 is temporarily attached to near the linkage member 184. The pull member 147 is dismounted from the movable ring 151, and the coil stopper 140 is dismounted from the back-end base 143. At this time, the pull member 147 and coil stopper 140 are dismounted or remounted by loosening or tightening the screws. The work is easy to do.

As shown in FIG. 19B, the hardness adjustment unit 200 including the coil 132 and wire 133 is removed through an emptied space in the operation unit, that is, a space where the cylindrical tube 145 has been placed. At this time, if the movable ring 151 interferes with the work, the movable ring 151 interferes with the work, the movable ring 151 shaped like the letter C may be dismounted from the component 204.

As mentioned above, the string 205 attached to the linkage member 184 is passed through the flexible tube 131.

Thereafter, a linkage member 184a of the new hardness adjustment unit 200a is, as shown in FIG. 19C, temporarily attached to the tip of the string 205 inserted into the emptied space in the operation unit 6. The hardness adjustment unit 200a includes a new coil 132a and wire 133a.

The string 2065 is, as shown in FIG. 19D, pulled to the space between the bendable part 22 in the distal part of the endoscope and the linkage tube 138. The new hardness adjustment unit 200a consisting of the linkage member 184a, wire 133a, coil 132a, pull member 147a, and stopper 149a is passed through the flexible tube 131.

Thereafter, a coil stopper 140a is screwed firmly to the back-end base 143, and the pull member 147a is screwed firmly to the movable ring 151. The string 205 is then detached from the linkage member 184a. The linkage member 184a is hung on to the linkage tube 138. The bendable part 22 is then placed on the linkage tube 138, whereby the linkage tube 138 is secured. Thereafter, all the components are assembled by reversing the procedure of disassembling.

When the hardness adjustment unit 200 is thrown away, the linkage member 184 may cut apart from the distal end of the wire 133. Instead of adopting the string 205, the cut end of the wire may be encapsulated with a heat-contractile tube. The heat-contractile tube is bound with the wire 133. The hardness adjustment unit 200 is then pulled out of the flexible tube. This eliminates the concern for the possibility that the linkage member 184 may be hooked over the inner wall of the flexible tube or any other component. When the new hardness adjustment unit 200a is passed through the flexible tube, it is passed without the linkage member 184a. After the new hardness adjustment unit 200a is passed, the linkage member 184a may be attached to the new hardness adjustment unit 200a and then hung on to the linkage tube 138.

As mentioned above, when the hardness adjustment unit 200 including the coil 132 and wire 133 is replaced with a new one, the component 204 need not be removed from the flexible tube 131. Supposing the component 204 were removed from the flexible tube 131, it would not be easy to rearrange the component 204 in the flexible tube 131 according to the layout shown in FIG. 16A.

In this embodiment, the hardness adjustment unit 200 including the coil 132 and wire 133 can be replaced with a new one by merely creating a small space. At this time, it is unnecessary to fully separate the distal part 21, bendable part 22, plastic tube 23, and operation unit 6 from one another. The work space may therefore be limited and the work is easy to do.

Moreover, the linkage tube 138 and back-end base 143 are united with the flexible tube 131. The hardness adjustment unit including the coil 132 and wire 133 can be separated readily from the linkage tube 138 and back-end base 143. The flexible tube 131 need not be replaced with a new one.

Moreover, the linkage member of the hardness adjustment unit including the coil 132 and wire 133, which links the hardness adjustment unit and endoscope 2, may be located in the middle of the flexible tube 131 away from the end thereof. In this case, the hardness adjustment unit cannot be dismounted from the endoscope 2 (or it is very hard to dismount the hardness adjustment unit). However, in this embodiment, the linkage member of the hardness adjustment unit 200 including the coil 132 and wire 133, which links the hardness adjustment unit and endoscope 2, is located near the end of the flexible tube 131. Dismounting and mounting can therefore be carried out easily.

Moreover, the back-end part of the hardness adjustment unit 200 can be separated from hardness adjustment manipulation members including the hardness adjustment knob 134 and cylinder 153. Herein, the hardness adjustment unit 200 includes the coil 132 and wire 133 and serves as a hardness adjusting means. Among the components realizing the hardness adjustment function, the hardness adjustment manipulation members need not be replaced with new ones. Consequently, the cost of repair can be minimized.

According to this embodiment, when it becomes necessary to replace a hardness adjusting means with a new one, the hardness adjusting means alone can be replaced with a new one relatively easily. Compared with the prior art, the amount of work required for replacement can be achieved easily and shortly. Moreover, only the hardness adjusting means will need to be replaced with a new one. Another merit lies in that the economic burden incurred by a user is small.

Moreover, a deteriorated coil and wire have their natural length varied. There is a possibility that the relative length of the coil and wire with respect to the natural length of a flexible tube may have changed from the initial length. There is some fear that an excess load may be imposed on the flexible tube. The deteriorated coil and wire can be dismounted whereby a new coil and wire can be mounted. The relative length with respect to the length of the flexible tube can thus be approached to the initial one (length before delivery). In other words, the coil and wire can be mounted in such a manner that they will not be pushed into the flexible tube excessively and tensed excessively in the flexible tube. Any excess load imposed on the flexible tube can therefore be reduced to the greatest possible extent. In particular, before the new hardness adjustment unit 200a is mounted, the wire 133a is left uncoupled from the linkage member 184a. The length of the wire 133a is shortened in accordance with the length of an actual flexible tube. The linkage member 184a is then attached to the wire 133a. A difference in length of an individual flexible tube from another can thus be accommodated. The relative length of the coil and wire with respect to the length of the flexible tube can be determined more accurately. Any excess load that may be imposed on the flexible tube can thus be reduced further.

According to this embodiment, the advantages described below can be provided.

The hardness adjusting means in the insertion unit 20 is structured so that it can be dismounted and remounted from and in the endoscope 2. When the function of the hardness adjusting means is degraded, the hardness adjusting means can be replaced with a new one relatively easily. This results in the endoscope 2 whose ability to adjust hardness can be maintained easily. In contrast, according to the prior art, since the hardness adjusting means cannot be separated from the flexible tube, time-consuming disassembly must be carried out in order to replace the hardness adjusting means with a new one.

Moreover, according to this embodiment, a mounting and dismounting member is included in the endoscope 2. Any operator (user) cannot tamper with the components of the endoscope 2. The quality provided by the manufacturer can be guaranteed.

The third embodiment of the present invention will be described with reference to FIG. 20 and FIG. 21.

Figure 20:
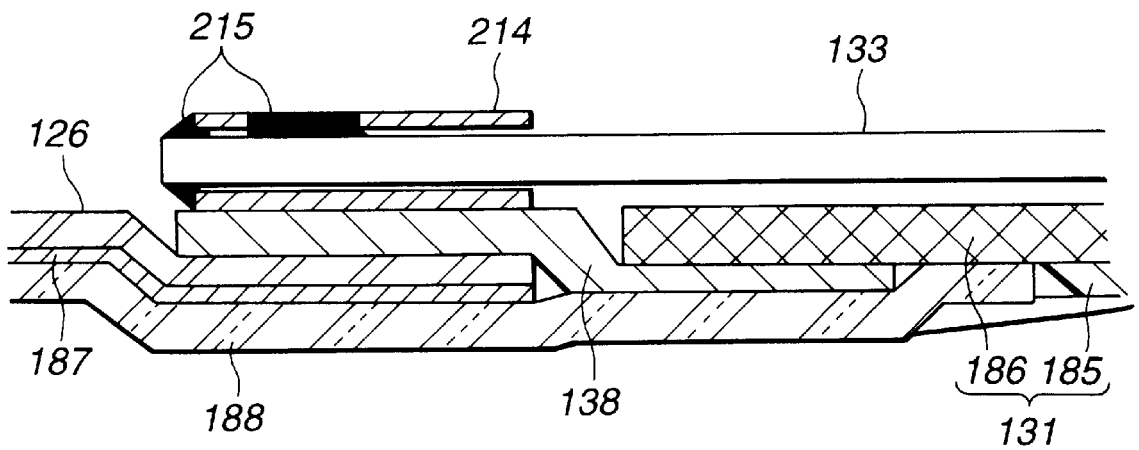
FIG. 20 and FIG. 21 are diagrams to be referred to for explaining the third embodiment.

As shown in FIG. 20, in this embodiment, a pipe 214 is fixed unitedly and firmly to the linkage tube 138 by means of a brazing filler or the like. The wire 133 is inserted into the pipe 214 and fixed to the pipe 214 by means of a securing means 215 such as a solder or adhesive.

In the vicinity of the pipe 214, the coil pipe 203 is, like the one shown in FIG. 14B, fixed firmly and unitedly to the linkage tube 138 by means of a brazing filler or the like. The coil pipe 203 encloses the angling wires 127. The securing means 215 is something that melts at a temperature considerably lower than the temperature at which the brazing filler melts, or that melts with a solvent.

Figure 21:
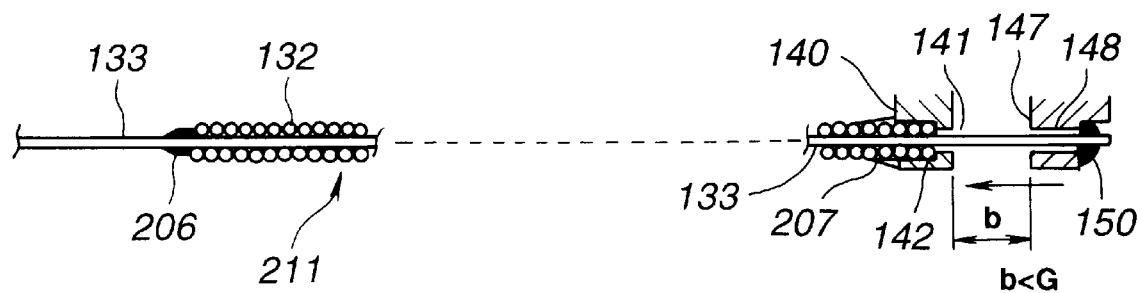

FIG. 21 shows the portion of the endoscope succeeding rearward the one shown in FIG. 20. The distal part of the coil 132 is secured to the distal part of the wire 133 by means of a brazing filler 206. Moreover, the back end of the wire 133 is firmly fixed to the pull member 147 by means of a brazing filler 150. However, in this embodiment, the stopper 149 is excluded.

FIG. 21 shows the natural state of the coil 132 and wire 133. At this time, the coil stopper 140 and pull member 147 are separated from each other by the gap b. The coil stopper and pull member are put in the operation unit 6 in the same manner as the coil stopper 140 and pull member 147 shown in FIG. 15. Specifically, the back end of the wire 133 is pushed into the coil 132. The associated members such as the pull member 147, movable ring 151, cam grooves 164a and 164b, and cam cylinder 153 are then put in the operation unit so that the gap will be substantially eliminated.

After these components are assembled, the coil 132 is stretched by a length corresponding to the gap b. The coil 132 is a coil having its wire wound densely in its natural original form. After the components are assembled as shown in FIG. 15, the coil 132 has a slight gap between adjoining turns of wire.

The distance corresponding to the gap b is shorter than a distance G in FIG. 15.

When the insertion unit 20 is straight, a difference G–d is a stroke (a range of hardness adjustment) by which the wire is pulled in order to apply a compressing force to the coil 132. The other components are identical to those of the second embodiment. The same reference numerals will be assigned to the same members. The description of these members will be omitted.

The operations of this embodiment will be described below.

In this embodiment, a hardness adjustment unit 211 including the coil 132 and wire 133 consists of four components alone; that is, the wire 133, coil 132, coil stopper 140, and pull member 147. The number of parts is smaller than that of the hardness adjustment unit 200 of the second embodiment. Not only the initial cost but also the cost of replacement is therefore lower.

According to the fixing method shown in FIG. 20, the pipe 214 and the coil pipe 203 located near the pipe 214 are secured by the brazing filler 201. The securing means 215 is, for example, a solder that melts apparently at a lower temperature than the brazing filler. When the pipe 214 is heated at the temperature, the wire 133 will come out of the pipe 214 but the pipe 214 and coil pipe 203 will not be freed from the linkage tube 138.

Over a predetermined time, for example, several seconds during which the heating is performed at the temperature, the other contents and pipe 214 are separated from one another by some distance to prevent the other contents from being injured. In this state, work is carried out within the linkage tube 138. Moreover, the flexible tube 131 is composed of the metallic tube 186 and armor 185. The metallic tube 186 is made mainly of a metal and constructed by putting spiral tubes or mesh tubes in layers. The armor 185 is made of a resin and placed on the metallic tube 186. During the heating, the distance of the armor 185 from the pipe 214, the heating temperature, and the heating time are determined in such a way that the armor 185 will not be melted.

Moreover, the securing means 215 may be an adhesive to be melted by a certain solvent. In this case, the materials of the components are determined in consideration of the following requirements: when the solvent is applied to the securing means 215, the pipe 214 and coil pipe 203 will not be freed from the linkage tube 138, and the other components and flexible tube 131 will not be injured.

The aforesaid hardness adjusting means may not be the means including the coil 132 and wire 133 but may be any other means utilizing a shape memory alloy or fluid pressure.

According to the present invention, it is apparent that a wide range of different embodiments can be constructed based on the invention without a departure from the spirit and scope of the invention. This invention is limited by the appended claims but not restricted by an specified embodiments.

What is claimed is:

1. An endoscope capable of varying the hardness of a flexible part of an insertion unit thereof, comprising:
   a hardness adjusting means, comprising an elongated coil and a wire disposed within the coil, for adjusting the hardness of the flexible part of the insertion unit; and
   a location changing means for changing the location of the coil and the wire in a longitudinal direction of the insertion unit, such that the hardness adjusting means will maintain the insertion unit hardness despite deterioration of the coil or the wire of the hardness adjusting means.

2. An endoscope capable of varying the hardness of a flexible part of an insertion unit thereof according to claim 1, wherein:
   the location changing means comprises a locking member fixed to the proximal end of the coil and a plurality of screws for fixing a location of the locking member;
   a plurality of recesses, in which the plurality of screws is disposed, extending in a longitudinal direction of the insertion unit near the flexible part; and
   a degraded functionality of the coil is compensated by changing the positions at which the screws are tightened.

3. An endoscope capable of varying the hardness of a flexible part of an insertion unit thereof according to claim 1, wherein:
   the location changing means is a spacer member for changing the position of the distal end of the wire; and
   the wire is corrected by placing the spacer member to change the position of the distal end of the wire.

4. An endoscope capable of varying the hardness of a flexible part of an insertion unit thereof according to claim 3, further comprising a plurality of spacer members in a plurality of sizes.

5. An endoscope capable of varying the hardness of a flexible part of an insertion unit thereof according to claim 1, wherein:
   the location changing means comprises a coil pitch adjustment member coupled to the proximal end of the coil; and
   the proximal end of the coil is turned relative to a fixed distal end of the coil by turning the coil pitch adjustment member, whereby the pitch of the coil is adjusted to correct for wire deterioration.

6. An endoscope capable of varying the hardness of a flexible part of an insertion unit thereof according to claim 5, wherein:
   the location changing means includes a locking member fixed to the proximal end of the coil and a plurality of screws used to fix the locking member in a position; and
   the locking member fixed to the proximal end of the coil is fixed in the position by tightening the screws.

7. An endoscope capable of varying the hardness of a flexible part of an insertion unit thereof according to claim 1, wherein the location changing means is located inside an outermost housing of the endoscope, and is located outside a tubular member enclosing various components in the flexible part.

8. An endoscope capable of varying the hardness of a flexible part of an insertion unit thereof according to claim 7, wherein:

a part of the outermost housing is capable of being opened and closed; and the part of the outermost housing is opened in order to adjust the positions of a plurality of screws included in the location changing means or to adjust the placement of a spacer, whereby correction is achieved.

9. An endoscope enabling variation of the hardness of a flexible part of an insertion unit thereof according to claim 1, wherein at least the coil and the wire included in the hardness adjusting means are integrated into a unit.

10. An endoscope enabling variation of the hardness of a flexible part of an insertion unit thereof according to claim 9, wherein the hardness adjusting means formed as a unit is removable from the endoscope so as to be replaceable with a new hardness adjusting means.

11. An endoscope enabling variation of the hardness of a flexible part of an insertion unit thereof, comprising:

a hardness adjusting means, composed of an elongated coil and a wire disposed within the coil, for adjusting the hardness of the flexible part of the insertion unit; and a unit mounting means for mounting the hardness adjusting means in the flexible part of the insertion unit so that the hardness adjusting means can be freely dismounted from the flexible part of the insertion unit.

12. An endoscope enabling variation of the hardness of a flexible part of an insertion unit thereof according to claim 11, wherein the mounting means is a mechanical structure for mechanically linking the distal part of the hardness adjusting means to the distal end of the flexible part, and the proximal part of the hardness adjusting means to the operation unit, and thus securing the distal part and proximal part of the hardness adjusting means.

13. An endoscope enabling variation of the hardness of a flexible part of an insertion unit thereof according to claim 11, wherein a member of the mounting means in the insertion unit and serving as the proximal part of the hardness adjusting means is separated from at least one member of an the operation unit of the endoscope.

14. An endoscope enabling variation of the hardness of a flexible part of an insertion unit thereof according to claim 11, wherein a member of the mounting means serving as the distal part of the hardness adjusting means is separated from a soft tube serving as an armor of the flexible part.

15. An endoscope enabling variation of the hardness of a flexible part of an insertion unit thereof according to claim 14, wherein when the member serving as the distal part of the hardness adjusting means is separated from the soft tube serving as the armor of the flexible part, components in the soft tube remain connected to the distal part and operation unit of the endoscope through the soft tube.

16. An endoscope enabling variation of the hardness of a flexible part of an insertion unit thereof according to claim 11, wherein at least the coil and the wire included in the hardness adjusting means are integrated into a unit.

17. An endoscope enabling variation of the hardness of a flexible part of an insertion unit thereof according to claim 16, wherein the hardness adjusting means formed as a unit is removable from the endoscope so as to be replaceable with a new hardness adjusting means.

* * * * *